(12) United States Patent  
Klaubert et al.

(10) Patent No.: US 9,487,520 B2  
(45) Date of Patent: Nov. 8, 2016

(54) COELENTERAZINE DERIVATIVES AND METHODS OF USING SAME

(75) Inventors: Dieter H. Klaubert, Arroyo Grande, CA (US); Poncho Meisenheimer, San Luis Obispo, CA (US); James Unch, Arroyo Grande, CA (US); Wenhui Zhou, Santa Maria, CA (US)

(73) Assignee: PROMEGA CORPORATION, Madison, WI (US)

( * ) Notice: Subject to any disclaimer, the term of this patent is extended or adjusted under 35 U.S.C. 154(b) by 0 days.

(21) Appl. No.: 13/287,519

(22) Filed: Nov. 2, 2011

(65) Prior Publication Data

US 2012/0107849 A1    May 3, 2012

Related U.S. Application Data

(60) Provisional application No. 61/409,413, filed on Nov. 2, 2010.

(51) Int. Cl.
| C07D 487/04 | (2006.01) |
| C07H 17/02  | (2006.01) |
| C12Q 1/66   | (2006.01) |

(52) U.S. Cl.
CPC ............. *C07D 487/04* (2013.01); *C07H 17/02* (2013.01); *C12Q 1/66* (2013.01)

(58) Field of Classification Search
CPC .................................................. C07D 487/04
See application file for complete search history.

(56) References Cited

U.S. PATENT DOCUMENTS

| 5,670,356 A | 9/1997 | Sherf et al. |
| 5,683,888 A | 11/1997 | Campbell |
| 5,837,465 A | 11/1998 | Squirrell et al. |
| 5,998,204 A | 12/1999 | Tsien et al. |
| 6,132,983 A | 10/2000 | Lowe et al. |
| 6,171,808 B1 | 1/2001 | Squirrell et al. |
| 6,265,177 B1 | 7/2001 | Squirrell et al. |
| 6,387,675 B1 | 5/2002 | Wood et al. |
| 6,544,754 B2 | 4/2003 | Inoye |
| 6,552,179 B1 | 4/2003 | Wood et al. |
| 6,602,677 B1 | 8/2003 | Wood et al. |
| 7,078,181 B2 | 7/2006 | Hawkins et al. |
| 7,108,996 B2 | 9/2006 | Hawkins et al. |
| 7,118,878 B1 | 10/2006 | Hawkins |
| 7,125,697 B2 | 10/2006 | Inoye |
| 7,238,842 B2 | 7/2007 | Wood et al. |
| 7,241,584 B2 | 7/2007 | Wood et al. |
| 7,268,229 B2 | 9/2007 | Wood et al. |
| 7,378,255 B2 | 5/2008 | Horn et al. |
| 7,416,854 B2 | 8/2008 | Riss et al. |
| 7,425,436 B2 | 9/2008 | Darzins et al. |
| 7,429,472 B2 | 9/2008 | Darzins et al. |
| 7,537,912 B2 | 5/2009 | Wood et al. |
| 7,553,632 B2 | 6/2009 | Niles et al. |
| 7,692,002 B2 | 4/2010 | Alberto et al. |
| 7,692,022 B2 | 4/2010 | Cali et al. |
| 7,728,118 B2 | 6/2010 | Wood et al. |
| 7,741,067 B2 | 6/2010 | Hawkins et al. |
| 7,807,402 B2 | 10/2010 | Horn et al. |
| 7,867,726 B2 | 1/2011 | Wood et al. |
| 7,879,540 B1 | 2/2011 | Wood et al. |
| 7,888,086 B2 | 2/2011 | Darzins et al. |
| 7,906,282 B2 | 3/2011 | Wood et al. |
| 7,906,298 B1 | 3/2011 | Squirrell et al. |
| 7,935,803 B2 | 5/2011 | Darzins et al. |
| 7,951,550 B2 | 5/2011 | Cali et al. |
| 8,003,350 B2 | 8/2011 | Fujii et al. |
| 8,008,006 B2 | 8/2011 | Wood et al. |
| 8,030,017 B2 | 10/2011 | Wood et al. |
| RE42,931 E | 11/2011 | Wood et al. |
| 8,106,052 B2 | 1/2012 | Wood et al. |

(Continued)

FOREIGN PATENT DOCUMENTS

| CN | 1075680 | 12/2005 |
| CN | 101287842 | 10/2008 |

(Continued)

OTHER PUBLICATIONS

Inoue et al. Chemical studies of myctophina fish bioluminescence, Chemistry Letters (1987), (2), 417-18.*
Mitani et al. Enhancement effect of 2,6-O-dimethyl-_-cyclodextrin on the chemiluminescent detection of _-D-galactosidase using a Cypridina luciferin analog Analytical Sciences (1995), 11(6), 1013-15.*
United States Patent Office Notice of Allowance for U.S. Appl. No. 13/287,992 dated Nov. 18, 2013 (12 pages).
United States Patent Office Notice of Allowance for U.S. Appl. No. 13/287,992 dated Apr. 1, 2014 (11 pages).

(Continued)

*Primary Examiner* — Brian McDowell
(74) *Attorney, Agent, or Firm* — Michael Best & Friedrich LLP

(57) ABSTRACT

The invention provides coelenterazine derivatives which are substrates for a non-luminescent enzyme and a pro-substrate for a luminescent enzyme. The invention also provides a method of using the derivatives. The derivatives are of Formula II:

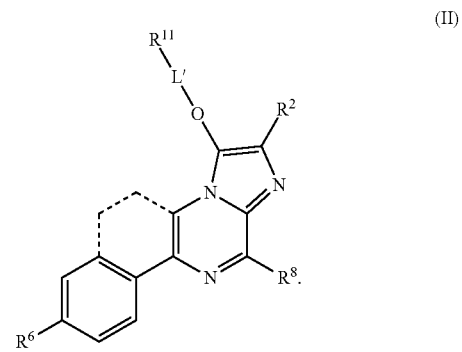

21 Claims, 10 Drawing Sheets

(56) References Cited

U.S. PATENT DOCUMENTS

| | | | |
|---|---|---|---|
| 8,168,405 B2 | 5/2012 | Darzins et al. |
| 8,183,007 B2 | 5/2012 | Zegzouti et al. |
| 8,183,036 B2 | 5/2012 | Fan et al. |
| 8,202,700 B2 | 6/2012 | Darzins et al. |
| 8,669,103 B2 | 3/2014 | Binkowski et al. |
| 2001/0046687 A1 | 11/2001 | Dicesare |
| 2003/0068801 A1 | 4/2003 | Wood et al. |
| 2003/0153090 A1 | 8/2003 | Wood et al. |
| 2003/0166905 A1 | 9/2003 | Wood et al. |
| 2003/0232404 A1 | 12/2003 | Wood et al. |
| 2004/0002127 A1 | 1/2004 | Inoue et al. |
| 2004/0096924 A1 | 5/2004 | Hawkins et al. |
| 2004/0096927 A1 | 5/2004 | Chittock et al. |
| 2004/0171099 A1 | 9/2004 | Cali et al. |
| 2004/0178545 A1 | 9/2004 | Cates |
| 2004/0214258 A1 | 10/2004 | Wood et al. |
| 2004/0224377 A1 | 11/2004 | Hawkins et al. |
| 2005/0026171 A1 | 2/2005 | Hawkins et al. |
| 2005/0153310 A1 | 7/2005 | Fan et al. |
| 2005/0164321 A1 | 7/2005 | Riss et al. |
| 2005/0272114 A1 | 12/2005 | Darzins et al. |
| 2006/0024808 A1 | 2/2006 | Darzins et al. |
| 2006/0051827 A1 | 3/2006 | Hawkins et al. |
| 2006/0068395 A1 | 3/2006 | Wood et al. |
| 2006/0127988 A1 | 6/2006 | Wood et al. |
| 2006/0183212 A1 | 8/2006 | Wood et al. |
| 2006/0234324 A1 | 10/2006 | Inouye et al. |
| 2007/0015790 A1 | 1/2007 | Cali et al. |
| 2007/0087400 A1 | 4/2007 | Darzins et al. |
| 2008/0026407 A1 | 1/2008 | Wood et al. |
| 2008/0050760 A1 | 2/2008 | Wood et al. |
| 2008/0070299 A1 | 3/2008 | Wood et al. |
| 2008/0090291 A1 | 4/2008 | Wood et al. |
| 2008/0145882 A1 | 6/2008 | Darzins et al. |
| 2008/0248511 A1 | 10/2008 | Daily et al. |
| 2008/0268482 A1 | 10/2008 | Riss et al. |
| 2008/0274488 A1 | 11/2008 | Darzins et al. |
| 2008/0299593 A1 | 12/2008 | Cali et al. |
| 2009/0017482 A1 | 1/2009 | Riss et al. |
| 2009/0023173 A1 | 1/2009 | Cali et al. |
| 2009/0098627 A1 | 4/2009 | Darzins et al. |
| 2009/0137019 A1 | 5/2009 | Wood et al. |
| 2009/0253131 A1 | 10/2009 | Wigdal et al. |
| 2009/0275051 A1 | 11/2009 | Niles et al. |
| 2009/0305280 A1 | 12/2009 | Binkowski et al. |
| 2009/0305353 A1 | 12/2009 | Fuji et al. |
| 2009/0311769 A1 | 12/2009 | Wood et al. |
| 2010/0047839 A1 | 2/2010 | Huang et al. |
| 2010/0075350 A1 | 3/2010 | Zegzouti et al. |
| 2010/0273186 A1 | 10/2010 | Wood et al. |
| 2010/0281552 A1 | 11/2010 | Encell |
| 2011/0003316 A1 | 1/2011 | Cali et al. |
| 2011/0039257 A1 | 2/2011 | Binkowski et al. |
| 2011/0081670 A1 | 4/2011 | Hawkins et al. |
| 2011/0171673 A1 | 7/2011 | Darzins et al. |
| 2011/0177540 A1 | 7/2011 | Squirrell et al. |
| 2011/0201024 A1 | 8/2011 | Wood et al. |
| 2011/0207195 A1 | 8/2011 | Darzins et al. |
| 2011/0283373 A1 | 11/2011 | Binkowski et al. |
| 2012/0009647 A1 | 1/2012 | Wood et al. |
| 2012/0034672 A1 | 2/2012 | Kim et al. |
| 2012/0058505 A1 | 3/2012 | Helms et al. |
| 2012/0107849 A1 | 5/2012 | Klaubert et al. |
| 2012/0117667 A1 | 5/2012 | Klaubert et al. |
| 2012/0174242 A1 | 7/2012 | Binkowski et al. |
| 2013/0130289 A1 | 5/2013 | Benink et al. |
| 2014/0093894 A1 | 4/2014 | Benink et al. |
| 2015/0064731 A1 | 3/2015 | Klaubert et al. |

FOREIGN PATENT DOCUMENTS

| | | |
|---|---|---|
| CN | 102459579 | 5/2012 |
| EP | 134108 | 3/1985 |
| EP | 0751996 | 1/2003 |
| EP | 1281762 A2 | 2/2003 |
| EP | 1148139 | 8/2004 |
| EP | 1131441 B1 | 11/2005 |
| EP | 1630231 A2 | 3/2006 |
| EP | 1894933 A2 | 3/2008 |
| EP | 689587 B1 | 4/2008 |
| EP | 1935980 A1 | 6/2008 |
| EP | 1935986 | 6/2008 |
| EP | 1451155 B1 | 7/2008 |
| EP | 1978091 A1 | 10/2008 |
| EP | 1978092 A1 | 10/2008 |
| EP | 1124944 | 12/2008 |
| EP | 1479763 | 12/2008 |
| EP | 2071023 A2 | 6/2009 |
| EP | 2071023 A8 | 6/2010 |
| EP | 1297337 | 1/2011 |
| EP | 2272972 | 1/2011 |
| EP | 2277872 | 1/2011 |
| EP | 2284271 A2 | 2/2011 |
| EP | 2298902 A1 | 3/2011 |
| EP | 2308978 A1 | 4/2011 |
| EP | 2325328 A1 | 5/2011 |
| EP | 2325329 A1 | 5/2011 |
| EP | 1546162 B1 | 6/2011 |
| EP | 2327768 A2 | 6/2011 |
| EP | 2341134 A2 | 7/2011 |
| EP | 2366777 A1 | 9/2011 |
| EP | 2366778 A1 | 9/2011 |
| EP | 2366779 A1 | 9/2011 |
| EP | 2366780 A1 | 9/2011 |
| EP | 2368976 A1 | 9/2011 |
| EP | 2368977 A1 | 9/2011 |
| EP | 2369006 A1 | 9/2011 |
| EP | 2374875 A2 | 10/2011 |
| EP | 2395078 A2 | 12/2011 |
| EP | 2395358 A2 | 12/2011 |
| EP | 2272973 | 1/2012 |
| EP | 2281046 B1 | 1/2012 |
| JP | 08-059686 | 3/1996 |
| JP | H08-294397 | 11/1996 |
| JP | 2000-197484 | 7/2000 |
| JP | 2001-516585 | 10/2001 |
| JP | 2002-320482 | 11/2002 |
| JP | 2003-512071 | 4/2003 |
| JP | 2005-245457 | 9/2005 |
| JP | 2005530485 | 10/2005 |
| JP | 2007097577 | 4/2007 |
| JP | 2008-532504 | 8/2008 |
| JP | 2009-532063 | 9/2009 |
| JP | 2010-507372 | 3/2010 |
| JP | 2014526443 | 10/2014 |
| WO | WO 95/18853 | 7/1995 |
| WO | WO 9525798 | 9/1995 |
| WO | WO 9607100 | 3/1996 |
| WO | WO 9622376 | 7/1996 |
| WO | WO 98/46729 | 10/1998 |
| WO | WO 9846739 | 10/1998 |
| WO | WO 9914336 | 3/1999 |
| WO | WO 00/24878 | 5/2000 |
| WO | WO 0120002 | 3/2001 |
| WO | WO 0131028 | 5/2001 |
| WO | WO 01/96862 | 12/2001 |
| WO | WO 02/16944 | 2/2002 |
| WO | WO 03/040100 | 5/2003 |
| WO | 2003/066611 | 8/2003 |
| WO | WO 2004027378 | 4/2004 |
| WO | WO 2004059294 | 7/2004 |
| WO | WO 2004072232 | 8/2004 |
| WO | WO 2004072299 | 8/2004 |
| WO | WO 2005038029 | 4/2005 |
| WO | WO 2005073722 | 8/2005 |
| WO | WO 2006/034061 | 3/2006 |
| WO | WO 2006093529 | 9/2006 |
| WO | WO 2006/130551 | 12/2006 |
| WO | WO 2007/120522 | 10/2007 |
| WO | WO 2008054821 | 5/2008 |
| WO | WO 2008086035 | 7/2008 |
| WO | WO 2008118445 A1 | 10/2008 |
| WO | WO 2008118445 A9 | 12/2008 |
| WO | WO 2009061413 | 5/2009 |

(56) References Cited

FOREIGN PATENT DOCUMENTS

| WO | WO 2009142735 | 11/2009 |
|---|---|---|
| WO | WO 2010011607 | 1/2010 |
| WO | WO 2010/119721 | 10/2010 |
| WO | WO 2010/127368 | 11/2010 |
| WO | WO 2011038219 | 3/2011 |
| WO | WO 2011143339 | 11/2011 |
| WO | WO 2012030960 | 3/2012 |
| WO | WO 2012/061477 | 5/2012 |
| WO | WO 2012/061529 | 5/2012 |
| WO | WO 2012/061530 | 9/2012 |
| WO | 2013/033515 | 3/2013 |

OTHER PUBLICATIONS

European Patent Office Action for Application No. 11785217.8 dated Apr. 11, 2014 (4 pages).
Chinese Patent Office Action for Application No. 201180052806.X dated Jul. 25, 2014 (17 pages, English translation included).
Singapore Written Opinion for Application No. 201303031-7 dated May 9, 2014 (9 pages).
Angelucci, F. et al., "Schistosoma mansoni fatty acid binding protein: specificity and functional control as revealed by crystallographic structure," Biochem. (2004) 43:13000-13011.
Arnold, K. et al., "The Swiss-Model workspace: a web-based environment for protein structure homology modelling," Bioinformatics (2006) 22(2):195-201.
Banaszynski et al., "Characterization of the FKBP-Rapamycin-FRB Ternary Complex" J. Am. Chem. Soc, 127(13):4715-4721(2005).
Becker, M.M. et al., "Gene cloning, overproduction and purification of a functionally active cytoplasmic fatty acid-binding protein (Sj-FABPc) from the human blood fluke Schistosoma japonicum," Gene (1994) 148:321-325.
Benezra et al., "The Protein Id: A Negative Regulator of Helix-Loop-Helix DNA Binding Proteins" Cell, 61(1):49-59(1990).
Berge et al., "Pharmaceutical Salts" J. Pharm. Sci., 66:1-19 (1977).
Burbelo et al., "Antibody-profiling technologies for studying humoral responses to infectious agents" Expert Review of Vaccines 9(6):567-578(2010).
Chenna et al., "Multiple sequence alignment with the Clustal series of programs" Nucl. Acids Res. 31(13):3497-3500 (2003).
Chothia et al., "The relation between the divergence of sequence and structure in proteins" EMBO J. 5(4):823-826 (1986).
Cowan, S.W. et al., "Crystallographic studies on a family of cellular lipophillic transport proteins," J. Mol. Biol. (1993) 230;1225-1246.
Daughtery, P.S. et al., "Quantitative analysis of the effect of the mutation frequency on the affinity maturation of single chain Fv antibodies," Proc. Natl. Acad. Sci. USA (2000) 97(5):2029-2034.
Dennell, R. et al., "Observations on the luminescence of bathypelagic crustacea decapoda of the Bermuda area," Zool. J. Linn. Soc., London (1955) XLII:393-406.
Esteves and Ehrlich. 2006. "Invertebrate Intracellular Fatty Acid Binding Proteins." Comparative Biochemistry and Physiology, Part C 142: 262-274.
Flower, D.R. et al., "A structural signature characteristic of the calycin protein superfamily," Protein Pept. Lett. (1995) 2(2):341-350.
Flower, D.R. et al., "Structure and sequence relationships in the lipocalins and related proteins," Protein Sci. (1993) 2:753-761.
Flower, D.R. et al., "The lipocalin protein family—structure and function," Biochem. J. (1996) 318:1-14.
Flower, D.R. et al., "The lipocalin protein family—structural and sequence overview," Biochimica et Biophysica Acta (2000) 1482:9-24.
Freifelder et al. "Synthesis of Primary 1,2-Diamines by Hydrogenation of alpha-Aminonitriles" Journal of the American Chemical Society, 82(3):696-698(1960).
Fujii, H. et al., "Increase in bioluminescence intensity of firefly luciferase using genetic modification," Anal. Biochem. (2007) 366:131-136.

Green, T et al., "Protective Groups in Organic Synthesis" Third Edition (1999).
Gross et al., "Real-time imaging of ligand-induced IKK activation in intact cells and in living mice" Nature Methods 2(8):607-614 (2005).
Gunasekaran et al. 2004. "Sequence and Structural Analysis of Cellular Retinoic Acid-Binding Proteins Reveals a Network of Conserved Hydrophobic Interactions." Proteins 54: 179-194.
Hagedorn et al., "Darstellung von a.&ungesattigten Isonitrilen, &Keto- und &Chlor-isonitrilen. Synthese des Xanthocillin-dimethylathers" Chem. Ber., 98:193(1965).
Head, J.F. et al., "The crystal structure of the photoprotein aequorin at 2.3A resolution," Nature (2000) 405:372-376.
Herring, P.J. et al., "Bioluminescence in crustacea," J. Crust. Biol. (1985) 5(4):557-573.
Herring, P.J. et al., "The spectral characteristics of luminous marine organisms," Proc. Royal Society London Series B. Biological Sciences (1983) 220(1219):183-217.
Herring, P.J., "Bioluminescence in decapod crustacea," J. Mar. Biol. Assoc. UK (1976) 156:1029-1047.
Inoue et al. "Squid bioluminescence. II. Isolation from Watasenia scintillans and synthesis of 2-(p-hydroxybenzyl)-6-(p-hydroxypheny1)-3,7-dihydroimidazo[1,2-a]pyrazin-3-one" Chem. Lett., 4(2):141-144 (1975).
Inoue, S. et al., "Complete structure of renilla luciferin and luciferyl sulfate," Tetra. Lett (1977) 31:2685-2688.
Inouye et al. "The Use of Renilla Luciferase, Oplophorus Luciferase, and Apoaequorin as Bioluminescent Reporter Protein in the Presence of Coelenterazine Analogues as Substrate" BBRC, 223:349-353 (1997).
Inouye, S. et al., "Overexpression, purification and characterization of the catalytic component of oplophorus luciferase in the deep sea shrimp," Protein Exp. Purification (2007) 56(2):261-268.
Inouye, S. et al., "Secretional luciferase of the luminous shrimp oplophorus gracilirostris: cDNA cloning of a novel imidazopyrazinone luciferase," FEBS Letts. (2000) 481:19-25.
Johnson, F.H. et al., "Introduction to the cypridina system," Meth. Enzym. (1978) 57:331-364.
Kabsch, W. et al., "Dictionary of protein secondary structure: pattern recognition of hydrogen-bonded and geometrical features," Biopolymers (1983) 22:2577-2637.
Kakoi et al., "A New Synthesis of Watasenia Preluciferin by Cyclization of 2-Amino-3-Benzyl-5-(p-Hydroxyphenyl)Pyrazine With p-Hydroxyphenylpyruviacc" Chem. Lett. 11(3):299-300 (1980).
Kakoi, "Synthesis of 2-Amino-3-benzyl-5-(p-hydroxyphenyl)pyrazine" Chem. Pharm. Bull., 50:301 (2002).
Karplus, K. et al., "Hidden Markov models for detecting remote protein homologies," Bioinformatics (1998) 14(10):846-856.
King, R.D. et al., "Identification and application of the concepts important for accurate and reliable protein secondary structure prediction," Protein Sci. (1996) 5:2298-2310.
Kishi et al., "The structure confirmation of the light-emitting moiety of bioluminescent jellyfish" Tetrahedron Lett. 13(27):2747(1972).
Kunkel, T.A., "Rapid and efficient site-specific mutagenesis without phenotypic selection," Proc. Natl. Acad. Sci. USA (1985) 82(2):488-492.
Kurowski, M.A. et al., "GeneSilico protein structure prediction meta-server," Nucl. Acids. Res. (2003) 31(13):3305-3307.
Langley et al., "Molecular Basis of O-Galactosidase a-Complementation PNAS (protein sequencing/protein conformation/deletion mutant)" 72:1254-1257 (1975).
Levit et al., "Ribonuclease S-Peptide—A Model for Molecular Recognition" J. Biol. Chem. 251:1333-1339 (1976).
Loening, A.M. et al., "Consensus guided mutagenesis of renilla luciferase yeilds enhanced stability and light output," Protein Eng. Des. Sel. (2006) 19(9):391-400.
Lorenz, W.W. et al., "Isolation and expression of a cDNA encoding renilla reinformis luciferase," Proc. Natl. Acad. Sci. USA (1991) 88:4438-4442.
Marcelino et al. 2006. "Evolutionary Coupling of Structural and Functional Sequence Information in the Intracellular Lipid-Binding Protein Family." Proteins 63: 373-384.

(56) References Cited

OTHER PUBLICATIONS

McGuffin, L.J. et al., "The PSIPRED protein structure prediction server," Bioinformatics (2000) 16(4):404-405.
Moroz et al., "Real-Time Imaging of HIF-1a Stabilization and Degradation" Plos One 4(4):e5077 (2009).
Mosrin et al., "Regio- and Chemoselective Multiple Functionalization of Chloropyrazine Derivatives. Application to the Synthesis of Coelenterazine" Organic Letters, 11:3406 (2009).
Murray, E.E. et al., "Codon usage in plant genes," Nucl. Acids. Res. (1989) 17(2):477-498.
Nakamura, H. et al., "Efficient bioluminescence of bisdeoxycoelenterazine with the luciferase of a deep-sea shrimp oplophorus," Tetra. Lett. (1997) 38(36):6405-6406.
Needleman, S.B. et al., "A general method applicable to the search for similarities in the amino acid sequence of two proteins," J. Mol. Biol. (1970) 48:443-453.
Nowel, M.S. et al., "Cuticular photophores of two decapod crustaceans, oplophorus spinosus and systellaspis debilis," Biol. Bull. (1998) 195:290-307.
Nowell et al. 1998. "Cuticular Photophores of Two Decapod Crustaceans, Oplophorus pinosus and Systellaspis." Biol. Bull. 195: 290-307.
Oba et al. 2009. "Biosynthesis of coelenterazine in the deep-sea copepod, Metridia pacifica. Biochem." Biophys. Res. Comm. 390: 684-688.
Ogbay et al. 2004. "The NMR Structure of a Stable and Compact All β-sheet Variant of Intestinal Fatty-Acid Binding Proteins." Protein Science 13: 1227-1237.
Ohana et al., "HaloTag7: A genetically engineered tag that enhances bacterial expression of soluble proteins and improves protein purification" Protein Expression and Purification, 68:110-120 (2009).
Paguio et al., "pGL4 Vectors: A New Generation fo Luciferase Reporter Vectors" Promega Notes, 89:7-10 (2005).
Parsons, M.R. et al., "Crystal structure of a quinoenzyme: copper amine oxidase of *Escherichia coli* at 2 A resolution," Structure (1995) 3:1171-1184.
Pearson, W.R. et al., "Improved tools for biological sequence comparison," Proc. Natl. Acad. Sci. USA (1988) 85:2444-2448.
Pichler, A. et al., "Imaging reversal of multidrug resistance in living mice with bioluminescence: MDR1 P-glycoprotein transports coelenterazine," Proc. Natl. Acad. Sci. USA (2004) 101(6):1702-1707.
Pollastri, G. et al., "Porter: a new, accurate server for protein secondary structure prediction," Bioinformatics (2005) 21(8):1719-1720.
Poupin, J., "Plancton marin bioluminescent," Rapport Scientifique du Leon (Sep. 1999) 1-83.
Raphael et al., "A novel method for multiple alignment of sequences with repeated and shuffled elements" Genome Res. 14(11):2336-2346 (2004).
Rea et al. 2009. "Mechanism of Ligand-Induced Folding of a Natively Unfolded Helixless Variant of Rabbit I-BABP." Biochemistry 48: 7556-7564.
Richardson and Richardson. 2002. "Natural β-sheet Proteins Use Negative Design to Avoid Edge-to-Edge Aggregation." PNAS 99(5): 2754-2479.
Schagat, T. et al., "KRX autoinduction protocol: a convenient metod for protein expression," Promega Notes (2008) 98:16-18.
Schultz, L.W. et al., "Crystal structure of a pH-regulated luciferase catalyzing the bioluminescent oxidation of an open tetrapyrrole," Proc. Natl. Acad. Sci. USA (2005) 102(5):1378-1383.
Shimomura et al. 1997. "Membrane Permeability of Coelenterazine Analogs Measured with Fish Eggs." Biochem J. 326: 297-298.
Shimomura, O. et al., "Properties and reaction mechanism of the bioluminescence system of the deep-sea shrimp oplophorus gracilorostris," Biochem. (1978) 17:994-998.
Shimomura, O. et al., "Semi-synthetic aequorins with improved sensitivity to CA2+ ions," Biochem. J. (1989) 261:913-920.

Sigrist et al., "Prosite, a protein domain database for functional characterization and annotation" Nucleic Acids Res. 38(suppl 1):D161-D166(2010).
Skerra, A., "Lipocalins as a scaffold," Biochem et Biophys. Acta (2000) 1482:337-350.
Skolnick, J. et al., "From genes to protein structure and function: novel applications of computational approaches in the genomic era," Trends in Biotech. (2000) 18:34-39.
Smathers and Petersen. 2011. "The Human Fatty Acid-Binding Protein Family: Evolutionary Divergences and Functions." Human Genomics 5(3): 170-191.
Smith, T.F. et al., "Identification of common molecular subsequences," J. Mol. Biol. (1981) 147:195-197.
Teranishi et al. 1990. "Synthesis and Chemiluminescence of Coelenterazine (Oplophorus Luciferin) Analogues." Bull. Chem. Soc. Jpn. 63: 3132-3140.
Thompson et al. 1995. "Crystal Structure of Cellular Retinoic Acid Binding Protein 1 Shows increased Access to the Binding Cavity Due to Formation of an Intermolecular β-sheet." J. Mol. Biol. 252: 433-446.
Thompson, E.M. et al., "Cloning and expression of cDNA for the luciferase from the marine ostracod Vargula hilgendorfii," Proc. Natl. Acad. Sci. USA (1989) 86:6567-6571.
Tramontano, "Comparative modelling techniques: where are we?" Genomics, 4:402-405 (2003).
Wada, K. et al., "Codon usage tabulated from the GenBank genetic sequence data," Nucl. Acids Res. (1990) 18(Supp):2367-2411.
Yamaguchi et al. 1975. "Oplophorus Oxyluciferin and a Model Luciferin Compound Biologically Active with Oplophorus Luciferase." Biochem. J. 151: 9-15.
Zhang et al., "A Universal Algorithm for Fast and Automated Charge State Deconvolution of Electrospray Mass-to-Charge Ratio Spectra" J. Am. Soc. Mass Spectrom., 9:225-233 (1998).
Zheng et al., "An efficient one-step site-directed and site-saturation mutagenesis protocol" Nucleic Acids Research, 32:e115 (2004).
Zuker et al., "Mfold web server for nucleic acid folding and hybridization prediction" Nucleic Acid Res. 31(13):3406-3415(2003).
International Search Report and Written Opinion for Application No. PCT/US2010/033449 dated Aug. 18, 2010 (12 pages).
International Search Report and Written Opinion for Application No. PCT/US2011/058924 dated Jan. 18, 2012 (8 pages).
International Search Report and Written Opinion for Application No. PCT/US2011/059017 dated Jan. 18, 2012 (8 pages).
International Search Report and Written Opinion for Application No. PCT/US2011/059018 dated Jul. 12, 2012 (15 pages).
United States Patent Office Action for U.S. Appl. No. 12/773,002 dated Dec. 29, 2011 (11 pages).
United States Patent Office Final Rejection for U.S. Appl. No. 12/773,002 dated Jun. 1, 2012 (17 pages).
United States Patent Office Final Rejection for U.S. Appl. No. 13/287,519 dated Apr. 24, 2013 (10 pages).
United States Patent Office Action for U.S. Appl. No. 13/287,992 dated Apr. 4, 2013 (9 pages).
European Patent Office Action for Application No. 11785217.8 dated Jun. 11, 2013 (15 pages).
United States Patent Office Final Rejection for U.S. Appl. No. 13/287,992 dated Jul. 11, 2013 (7 pages).
Shimomura, O. et al., "Semi-synthetic aequorin. An improved tool for the measurement of calcium concentration," Biochemical Journal, 1988, vol. 251, No. 2, pp. 405-410.
Israel Patent Office Action for Application No. 225869 dated Jan. 27, 2015 (12 pages).
Chinese Patent Office Action for Application No. 201180052806.X dated Dec. 26, 2014 (5 pages, English translation only).
Singapore Intellectual Property Office Written Opinion for Application No. 2013030317 dated Dec. 12, 2014 (12 pages).
United States Patent Office Action for U.S. Appl. No. 14/461,610 dated Feb. 3, 2015 (15 pages).
Fieser, L., et al., "Fieser and Fieser's Reagents for Organic Synthesis," John Wiley and Sons (1994).
Goto, Pure and Applied Chemistry (1968), 17(3-4), pp. 421-441.

(56) References Cited

OTHER PUBLICATIONS

Greene, T.W., et al., "Protective Groups in Organic Synthesis," 2d. Ed., John Wiley and Sons (1991).
Huang, S., et al., "Synthesis of a new long-wavelength latent fluorimetric indicator for analytes determination in the DT-Diaphorase coupling dehydrogenase assay system," Bionsensors & Bioelectronics, 2008, 23(12), pp. 1793-1798.
International Union of Pure and Applied Chemistry "Definitive Rules for Nomenlature of Organic Chemistry" J. Am. Chem. Soc. 1960, 82, 5545-5574.
Larock, R., "Comprehensive Organic Transformations, A Guide to Functional Group Preparation"s VCH Publishers (1989).
Oxford Dictionary of Biochemistry and Molecular Biology. Diaphorase. Oxford University Press. Second Edition. 2006. The General Editors. New York, New York, p. 178.
Paquette, L., ed., "Encyclopedia of Reagents for Organic Synthesis," John Wiley and Sons (1995).
Paquette, Leo A.; "Principles of Modem Heterocyclic Chemistry" (W.A. Benjamin, New York, 1968), particularly Chapters 1, 3, 4, 6, 7, 9.
Silvers, W.C., et al., "Shedding light by cancer redox—human NAD(P)H: quinone oxidoreductase 1 activation of a cloaked fluorescent dye" Chemical Communications, vol. 47, 2011, 11264-11266.
Weissberger, A., ed., "The Chemistry of Heterocyclic Compounds, A Series of Monographs," (John Wiley & Sons, New York, 1950 to present), in particular vols. 13, 14, 16, 19, and 28.
PCT/US2012/053310 International Search Report and Written Opinion dated Dec. 18, 2012 (13 pages).
United States Patent Office Action for U.S. Appl. No. 13/600,579 dated Apr. 28, 2014 (19 pages).
United States Patent Office Action for U.S. Appl. No. 13/600,579 dated Jun. 6, 2014 (21 pages).
United States Patent Office Action for U.S. Appl. No. 13/600,579 dated Mar. 12, 2015 (12 pages).
United States Patent Office Action for U.S. Appl. No. 13/600,579 dated Oct. 24, 2013 (15 pages).
United States Patent Office Action for U.S. Appl. No. 14/032,420 dated Mar. 25, 2015 (19 pages).
United States Patent Office Final Rejection for U.S. Appl. No. 13/600,579 dated Nov. 14, 2014 (14 pages).
Hawkins, et al., "Bright Light, No Lysis," Promega, 2005, pp. 10-14.
Mitani, M. et al., "Chemiluminescent assay of beta-D-galactosidase using cypridina luciferin analogue: 3-(Beta-D-galactopyranosyloxy)-6-(4-methoxyphenyl)-2-methyl-imidazol[1,2-alpha]pyrazine," Anal. Sci. (1994) pp. 813-814.
United States Patent Office Action for U.S. Appl. No. 14/032,420 dated Aug. 12, 2015 (19 pages).
Japanese Patent Office Action for Application No. 2013-537779 dated Jul. 8, 2015 (21 pages, including translation).
Chinese Patent Office Action for Application No. 201180052806.X dated Sep. 6, 2015 (14 pages, including translation).
Kondo, et al., "Novel synthetic route of coelenterazines -2-: Synthesis of various dehydrocoelenterazine analogs," Heterocycles, 2005, vol. 65, No. 4, pp. 843-856.
Saito, et al., "Substituent effects on the chemiluminescent properties of coelenterazine analogs," Chemistry Letters, 1998, vol. 1, pp. 95-96.
United States Patent Office Notice of Allowance for U.S. Appl. No. 14/461,610 dated May 15, 2015 (9 pages).
United States Patent Office Final Rejection for U.S. Appl. No. 131600,579 dated Jun. 26, 2015 (14 pages).
Mitani et al., "Enhancement effect of 2, 6-O-dimethyl-cyclodextrin on the chemiluminescent detection of -D-galactosidase using a Cypridina luceferin analog" Analytical Sciences (1995) 11(6), 1013-1015.

Chakravarty et al. "Accuracy of structure-derived properties in simple comparative models of protein structures". Nucleic Acid Research 2009 33(1): 244-259.
Todd et al. "Evolution of function in protein superfamilies' from a structural perspective". J. Mol. Biol. 2001. 307:1113-1143.
Wells, J.A. "Additivity of mutational effects in proteins". Perspectives in Biotechnology, American Chemical Society. Sep. 18, 1990. 29(37): 8509-8517.
Australian Patent Office Examination Report 1 for Application No. 2010242771 dated Jun. 5, 2014 (3 pages).
Chinese Patent Office Action for Application No. 201080019477.4 dated Nov. 7, 2013 (8 pages, English translation included).
Chinese Patent Office Action for Application No. 201080019477.4 dated Jul. 7, 2014 (6 pages, English translation included).
European Patent Office Action for Application No. 10717013.6 dated Nov. 7, 2013 (4 pages).
European Extended Search Report for Application No. 15186652.2 dated Jan. 5, 2016 (5 pages).
Japanese Patent Office Action for Application No. 2012-508822 dated Jul. 23, 2015 (12 pages, English translation included).
Japanese Patent Office Action for Application No. 2012-508822 dated Sep. 29, 2014 (19 pages, English translation included).
Korean Patent Office Action for Application No. 10-2011-7028749 dated Dec. 15, 2015 (16 pages, English translation included).
Singapore Patent Office Action for Application No. 2011074242 dated Nov. 20, 2015 (14 pages).
Singapore Patent Office Action for Application No. 2011074242 dated Dec. 31, 2014 (16 pages).
United States Patent Office Restriction Requirement for Application No. 12/773,003 dated Oct. 28, 2011 (19 pages).
United States Patent Office Action for U.S. Appl. No. 14/053,252 dated Jul. 31, 2015 (19 pages).
United States Patent Office Restriction Requirement for U.S. Appl. No. 14/053,252 dated May 22, 2015 (6 pages).
Australian Patent Office Action for Application No. 2011323419 dated Apr. 29, 2015 (4 pages).
Canadian Patent Office Action for Application No. 2,817,102 dated Feb. 5, 2015 (5 pages).
Chinese Patent Office Action for Application No. 201180063659.6 dated Aug. 27, 2014 (12 pages, English translation included).
Chinese Patent Office Action for Application No. 201180063659.6 dated Feb. 3, 2015 (9 pages, English translation included).
Chinese Patent Office Action for Application No. 201180063659.6 dated Apr. 20, 2015 (10 pages, English translation included).
Japanese Patent Office Action for Application No. 2013-537800 dated Oct. 19, 2015 (6 pages, English translation included).
Korean Patent Office Action for Application No. 10-2013-7014102 dated Sep. 25, 2014 (13 pages, English translation included).
Singapore Patent Office Action for Application No. 2013033675 dated Feb. 4, 2016 (10 pages).
United States Patent Office Action for U.S. Appl. No. 13/287,986 dated Feb. 20, 2013 (6 pages).
United States Patent Office Restriction Requirement for U.S. Appl. No. 13/287,986 dated Nov. 28, 2012 (6 pages).
United States Patent Office Action for U.S. Appl. No. 14/160,278 dated Nov. 19, 2015 (14 pages).
United States Patent Office Restriction Requirement for U.S. Appl. No. 14/160,278 dated Jan. 7, 2015 (6 pages).
United States Patent Office Action for U.S. Appl. No. 14/160,282 dated Mar. 27, 2015 (32 pages).
United States Patent Office Restriction Requirement for U.S. Appl. No. 14/160,282 dated Jan. 6, 2015 (5 pages).
United States Patent Office Notice of Allowance for U.S. Appl. No. 13/600,579 dated Oct. 21, 2015 (12 pages).
Chinese Patent Office Action for Application No. 201180052806.X dated May 12, 2016 (18 pages, including translation).
Israeli Patent Office Action for Application No. 225869 dated May 26, 2016 (5 pages including statement of relevance).
Australian Patent Office Examination Report for Application No. 2011323455 dated Jul. 15, 2016 (3 pages).

* cited by examiner each R is independently H, halogen or NO$_2$
each R$_2$ is independently H or Me
each X is independently NH, NMe, O or S

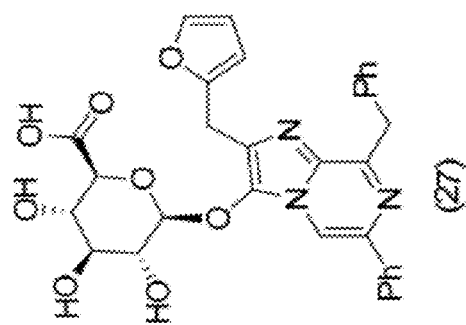
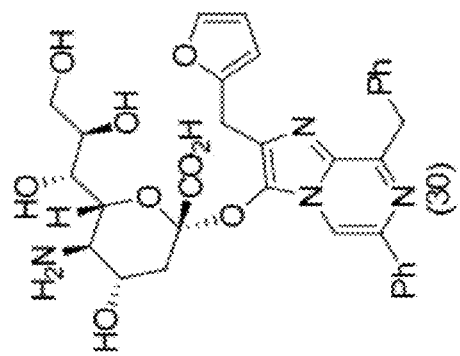
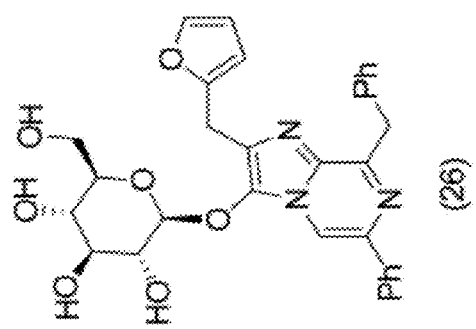
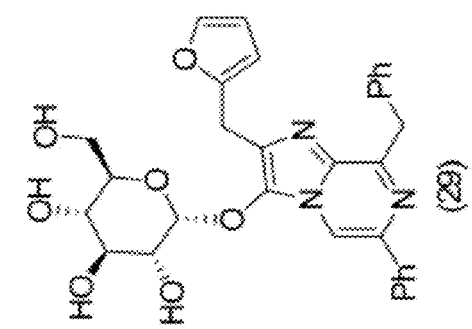
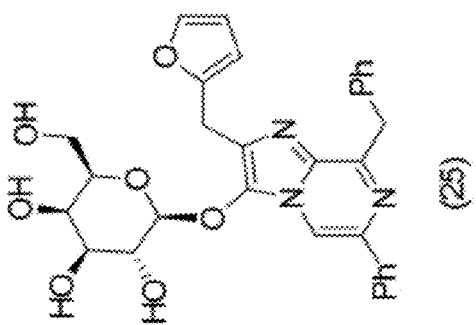
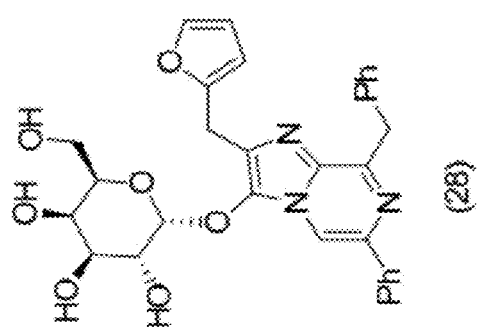
FIG. 5

| Substrate | Enzyme |
|---|---|
| Asp-Glu-Val-Asp | Caspases 3/7 |
| Leu-Glu-Thr-Asp | Caspase 8 |
| Leu-Glu-His-Asp | Caspase 9 |
| Val-Asp-Val-Ala-Asp | Caspase 2 |
| Gly-Pro | Dipeptidyl peptidase 4 (DPPIV) |
| Val-Pro | Dipeptidyl peptidase 4 (DPPIV) |
| Leu-Leu-Val-Tyr | Calpain and Chymotrypsin-like proteasome |
| Gln-Glu-Val-Tyr | Calpain and Chymotrypsin-like proteasome |
| Leu-Arg-Arg | Trypsin-like proteasome |
| norLeu-Pro-norLeu-Asp | Caspase-like proteasome |
| Ileu-Glu-Pro-Asp | Granzyme B |
| Ileu-Glu-Thr-Asp | Granzyme B or Caspase 6 |
| Phe-Arg | Cathepsins B/L |
| Leu-Arg | Cathepsin K |
| Gly-Pro-Arg | Thrombin |
| Gly-Gly-Arg | Thrombin |
| Lys | Trypsin |
| Ala-Ala-Phe | Aminopeptidase |
| Thr-Ser-Ala-Val-Leu-Gln | SARS protease |
| Val-Asn-Ser-Thr-Leu-Gln | SARS protease |

FIG. 6

| | |
|---|---|
| VP-coelenterazine | Boc-VPR-coelenterazine |
| Z-QEVY-coelenterazine | Z-PRNK-coelenterazine |
| Z-IEPD-coelenterazine | M-coelenterazine |
| Z-IETD-coelenterazine | L-coelenterazine |
| Z-FR-coelenterazine | Z-AGR-coelenterazine |
| Z-LR-coelenterazine | Z-RRVR-coelenterazine |
| Z-GPR-coelenterazine | Ac-PAL-coelenterazine |
| Z-GGR-coelenterazine | Ac-ANW-coelenterazine |
| Ac-K-coelenterazine | Z-LPSR-coelenterazine |
| Z-TSAVLQ-coelenterazine | Z-QTGG-coelenterazine |
| Z-VNSTLQ-coelenterazine | Ac-QTGG-coelenterazine |
| Ac-RLR-coelenterazine | Z-HLVLRLGG-coelenterazine |
| Z-LSTR-coelenterazine | Ac-LRSR-coelenterazine |
| Boc-LSTR-coelenterazine | Z-WEHD-coelenterazine |
| Suc-AAPF-coelenterazine | Z-STFAQP-coelenterazine |
| Z-ATAD-coelenterazine | Boc-QAR-coelenterazine |
| Z-IVLD-coelenterazine | Ac-OPR-coelenterazine |

FIG. 7

COELENTERAZINE DERIVATIVES AND METHODS OF USING SAME

CROSS-REFERENCE TO RELATED APPLICATIONS

This application claims the priority of U.S. Ser. No. 61/409,413, filed Nov. 2, 2010, which is incorporated herein by reference.

FIELD OF THE INVENTION

The present invention provides compounds and methods for assaying the presence and activity of enzymes.

BACKGROUND

The presence and activity of enzymes can be used to determine the health or metabolic state of a cell. Enzymes can also be markers for a particular cell type since the occurrence and activity of certain enzymes is frequently characteristic of a particular cell. For instance, the activity of certain enzymes can often be used to distinguish cells of bacterial, plant or animal origin or to distinguish the identity of tissue from which the enzyme originates.

Glycosidases, also know as glycoside hydrolases, catalyze the hydrolysis of the glycosidic linkage to generate two smaller sugars. They are extremely common enzymes with roles in nature including degradation of biomass such as cellulose and hemicellulose, in anti-bacterial defense strategies (e.g. lysozyme), in pathogenesis mechanisms (e.g., viral neuraminidases) and in normal cellular function (e.g. trimming mannosidases involved in N-linked glycoprotein biosynthesis). In bacteria and prokaryotes, glycosidases are found both as intracellular and extracellular enzymes that are largely involved in nutrient acquisition. One of the important occurrences of glycosidases in bacteria is the enzyme beta-galactosidase (LacZ), which is involved in the regulation of expression of the lac operon in *E. coli*. In higher organisms, glycosidases are found within the endoplasmic reticulum and Golgi apparatus where they are involved in processing of N-linked glycoproteins, and in the lysozome as enzymes involved in the degradation of carbohydrate structures. Deficiency in specific lysosome glycosidases can lead to a range of lysosomal storage disorders that result in development problems or death. Glycosidases are involved in the biosynthesis and degradation of glycogen in the body. Together with glycosyltransferases, glycosidases form the major catalytic machinery for the synthesis and breakage of glycosidic bonds.

Diaphorases are a ubiquitous class of flavin-bound enzymes that catalyze the reduction of various compounds, which act as hydrogen acceptors, from the reduced form of di- and triphosphopyridine nucleotides, i.e., NADH, NADPH. Cellular energy metabolism is a complex process that allows cells to store energy through a series of enzymatic and chemical reactions. One essential aspect of cellular energy metabolism is the reduction-oxidation state of the cell. The metabolic status of live cells as well as the assaying of enzyme activity and/or metabolite level can be determined by measuring the redox defining co-factor NAD(P)/NAD(P)H.

SUMMARY

In one aspect, the present invention provides a compound of formula (I):

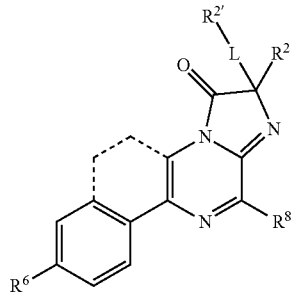

wherein $R^2$ is $-(CH_2)_n-T$ or $C_{1-5}$ alkyl;

$R^{2'}$ is selected from the group consisting of a peptide, an amino acid, a saccharide, $-O-R^A$, $-OC(O)O-R^A$, $-N(R^B)_2$, or $-NHC(O)OR^A$;

$R^6$ is selected from the group consisting of $-H$, $-OH$, $-NH_2-OC(O)R$ or $-OCH_2OC(O)R$;

$R^8$ is selected from the group consisting of

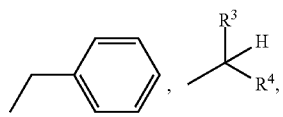

H or lower cycloalkyl;

wherein $R^3$ and $R^4$ are both H or both $C_{1-2}$ alkyl;

$R^A$ is $C_{1-4}$ alkyl, substituted $C_{1-4}$ alkyl, $-CH_2-R^C$ or $-CH_2-V-R^C$;

each $R^B$ is independently $-H$ or $-R^A$;

$R^C$ is aryl, heteroaryl, substituted aryl or substituted heteroaryl;

L is a linker;

n is 0 to 3;

each R is independently a $C_{1-7}$ alkyl;

T is aryl, heteroaryl, substituted aryl, substituted heteroaryl or cycloalkyl;

V is $-S-$ or $-O-$; and the dashed bonds indicate the presence of an optional ring, which may be saturated or unsaturated.

In another aspect, the present invention provides a compound of formula (II):

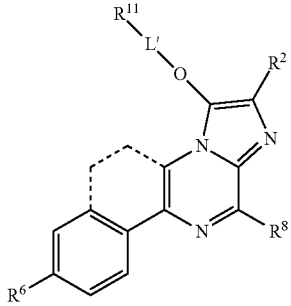

wherein $R^2$ is $-(CH_2)_n-T$ or $C_{1-5}$ alkyl;

$R^6$ is selected from the group consisting of $-H$, $-OH$, $-NH_2$, $-OC(O)R$ or $-OCH_2OC(O)R$;

$R^8$ is selected from the group consisting of

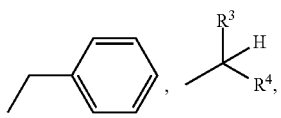

H or lower cycloalkyl;
$R^{11}$ is selected from the group consisting of a peptide, an amino acid, a saccharide, —O—$R^A$, —OC(O)O—$R^A$, —N($R^B$)$_2$, or —NHC(O)O$R^A$;
wherein $R^3$ and $R^4$ are both H or both $C_{1-2}$ alkyl;
$R^A$ is $C_{1-4}$ alkyl, substituted $C_{1-4}$ alkyl, —CH$_2$—$R^C$ or —CH$_2$—V—$R^C$;
each $R^B$ is independently —H or —$R^A$;
$R^C$ is aryl, heteroaryl, substituted aryl or substituted heteroaryl;
L' is a direct bond or a linker;
n is 0 to 3;
each R is independently a $C_{1-7}$ alkyl;
T is aryl, heteroaryl, substituted aryl, substituted heteroaryl or cycloalkyl;
V is —S— or —O—; and
the dashed bonds indicate the presence of an optional ring, which may be saturated or unsaturated.

In a further aspect, the present invention provides a compound of formula (III):

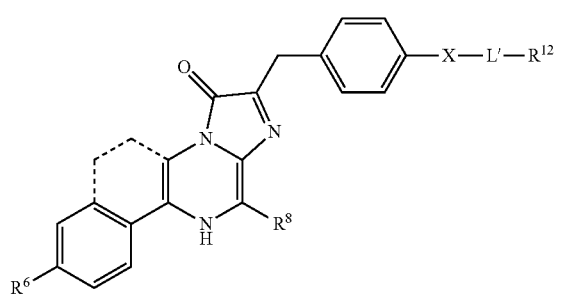

(III)

wherein $R^6$ is selected from the group consisting of —H, —OH, —NH$_2$—OC(O)R or —OCH$_2$OC(O)R;
$R^8$ is selected from the group consisting of

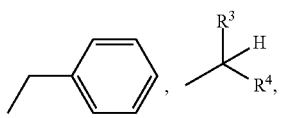

H or lower cycloalkyl;
$R^{12}$ is selected from the group consisting of a peptide, an amino acid, a saccharide, —O—$R^A$, —OC(O)O—$R^A$, —N($R^B$)$_2$, or —NHC(O)O$R^A$;
wherein $R^3$ and $R^4$ are both H or both $C_{1-2}$ alkyl;
$R^A$ is $C_{1-4}$ alkyl, substituted $C_{1-4}$ alkyl, —CH$_2$—$R^C$ or —CH$_2$—V—$R^C$;
each $R^B$ is independently —H or —$R^A$;
$R^C$ is aryl, heteroaryl, substituted aryl or substituted heteroaryl;
L' is a direct bond or a linker;
V is —S— or —O—;

each X is independently —S—, —O— or —NH—;
each R is independently $C_{1-7}$ alkyl; and
the dashed bonds indicate the presence of an optional ring, which may be saturated or unsaturated.

In another aspect, the present invention provides a compound of formula (IV):

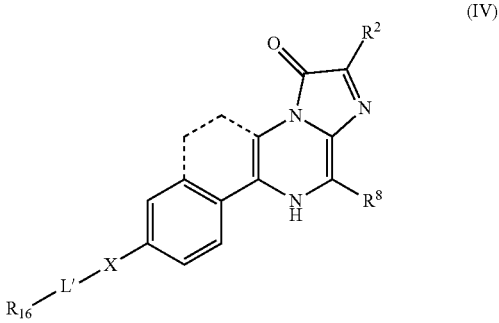

(IV)

wherein $R^2$ is —(CH$_2$)$_n$-T or $C_{1-5}$ alkyl;
$R^8$ is selected from the group consisting of

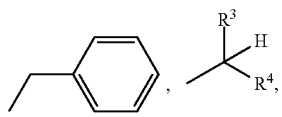

H or lower cycloalkyl;
$R^{16}$ is selected from the group consisting of a peptide, an amino acid, a saccharide, —O—$R^A$, —OC(O)O—$R^A$, —N($R^B$)$_2$, or —NHC(O)O$R^A$.
wherein $R^3$ and $R^4$ are both H or both $C_{1-2}$ alkyl;
$R^A$ is $C_{1-4}$ alkyl, substituted $C_{1-4}$ alkyl, —CH$_2$—$R^C$ or —CH$_2$—V—$R^C$;
each $R^B$ is independently —H or —$R^A$;
$R^C$ is aryl, heteroaryl, substituted aryl or substituted heteroaryl;
L' is a direct bond or a linker;
n is 0 to 3;
T is aryl, heteroaryl, substituted aryl, substituted heteroaryl or cycloalkyl;
V is —S— or —O—;
each X is independently —S—, —O— or —NH—;
each R is independently $C_{1-7}$ alkyl; and
the dashed bonds indicate the presence of an optional ring, which may be saturated or unsaturated.

The present invention also provides methods of using the above compounds.

BRIEF DESCRIPTION OF THE DRAWINGS

FIG. 5 shows examples of pro-coelenterazine saccharides useful in glycosidase assays.
FIG. 6 shows various peptidyl substrates for enzymes.
FIG. 7 shows suitable pro-coelenterazines for use in protease assays.

DETAILED DESCRIPTION

Figure 1:
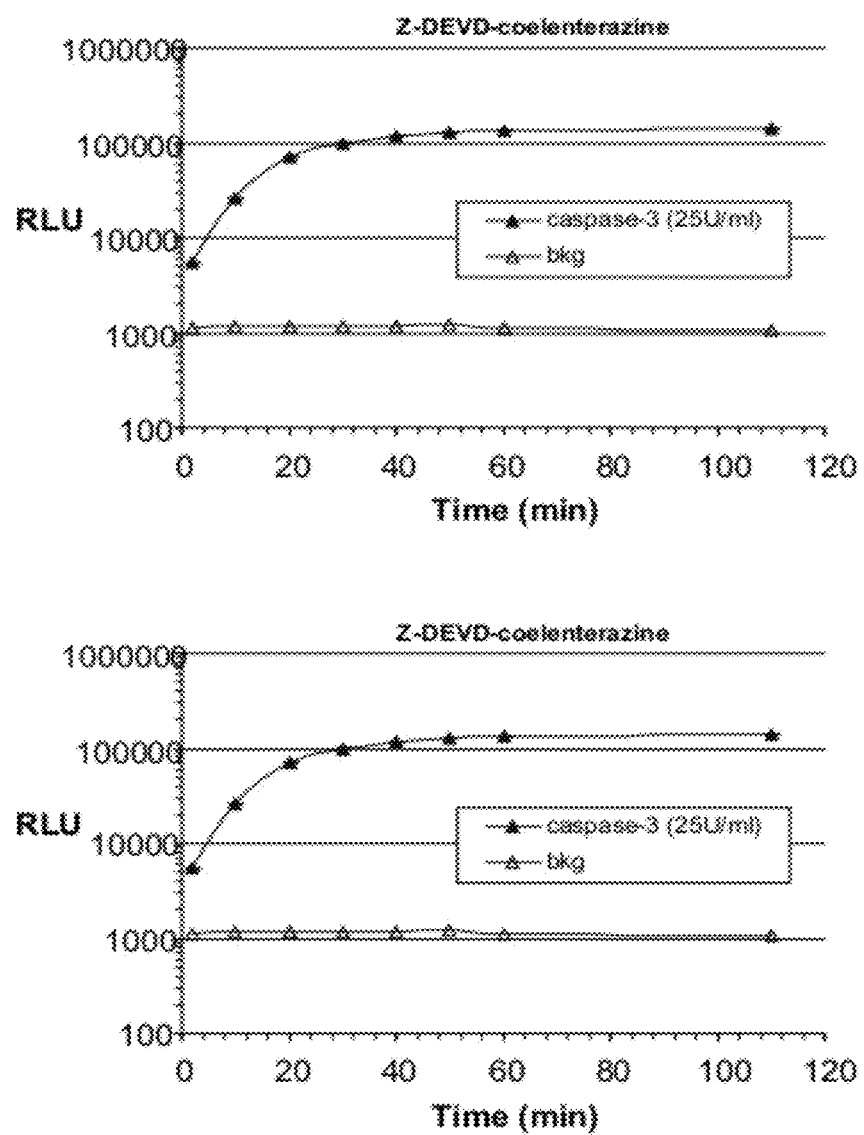
FIG. 1 shows the results of biological testing of z-DEVD-coelenterazine-h.

The present invention provides compounds and methods for assaying the presence and activity of various enzymes in a sample.

Unless expressly specified otherwise, the term "comprising" is used in the context of the present application to indicate that further members may optionally be present in addition to the members of the list introduced by "comprising". It is, however, contemplated as a specific embodiment of the present invention that the term "comprising" encompasses the possibility of no further members being present, i.e. for the purpose of this embodiment "comprising" is to be understood as having the meaning of "consisting of".

As used herein, the following terms and expressions have the indicated meanings. It will be appreciated that the compounds of the present invention contain asymmetrically substituted carbon atoms and may be isolated in optically active or racemic forms. It is well known in the art how to prepare optically active forms, such as by resolution of racemic forms or by synthesis from optically active starting materials. All chiral, diastereomeric, racemic forms and all geometric isomeric forms of a structure are part of this invention.

Specific values listed below for radicals, substituents, and ranges, are for illustration only. They do not exclude other defined values or other values within defined ranges for the radicals and substituents.

Definitions

The term "alkyl" refers to a monovalent moiety obtained by removing a hydrogen atom from a hydrocarbon compound. An alkyl group may contain from 1-30 carbon atoms, or 1-12 carbon atoms, or 1-10 carbon atoms or 1-6 carbon atoms or 1-4 carbon atoms. The alkyl group may be a straight-chain or branched and may be saturated, partially unsaturated, or fully unsaturated. An alkyl group may be optionally substituted with, for example, halo. Examples of straight-chain alkyl groups include, but are not limited to, ethyl, n-propyl, n-butyl, and n-propyl, n-hexyl and n-heptyl. Examples of straight-chain unsaturated alkyl groups which have one or more carbon-carbon double bonds include, but are not limited to, ethenyl (vinyl, —CH═CH$_2$), 2-propenyl (allyl, —CH—CH═CH$_2$), and butenyl. Examples of unsaturated alkyl which have one or more carbon-carbon triple bonds include, but are not limited to, ethynyl and 2-propynyl (propargyl). Examples of branched alkyl groups include isopropyl, iso-butyl, sec-butyl, t-butyl and iso-pentyl.

The term "amino acid" refers to both natural and unnatural amino acids. It also includes protected natural and unnatural amino acids.

The term "aryl" refers to a monovalent moiety obtained by removing a hydrogen atom from an aromatic ring. An aryl group may have from 6-10 carbon atoms ($C_{6-10}$ aryl). For example, the aryl group may be phenyl or naphthyl.

The term "halo" refers to a halogen, such as Cl, F, Br or I.

The term "heteroaryl" refers to a monovalent moiety obtained by removing a hydrogen atom from a heteroaromatic ring. A heteroaromatic ring may have from 5-10 ring atoms ($C_{5-10}$ heteroaryl (The use of "C" is understood to mean the total number of ring atoms regardless of whether the atom is C, N, O, or S).). The ring atoms may be carbon, nitrogen, sulfur or oxygen. More than one heteroatom may be present in the ring. For example, the heteroaryl group may be furyl, thienyl, thiazolyl, pyrazolyl, triazolyl or tetrazolyl.

Figure 3:
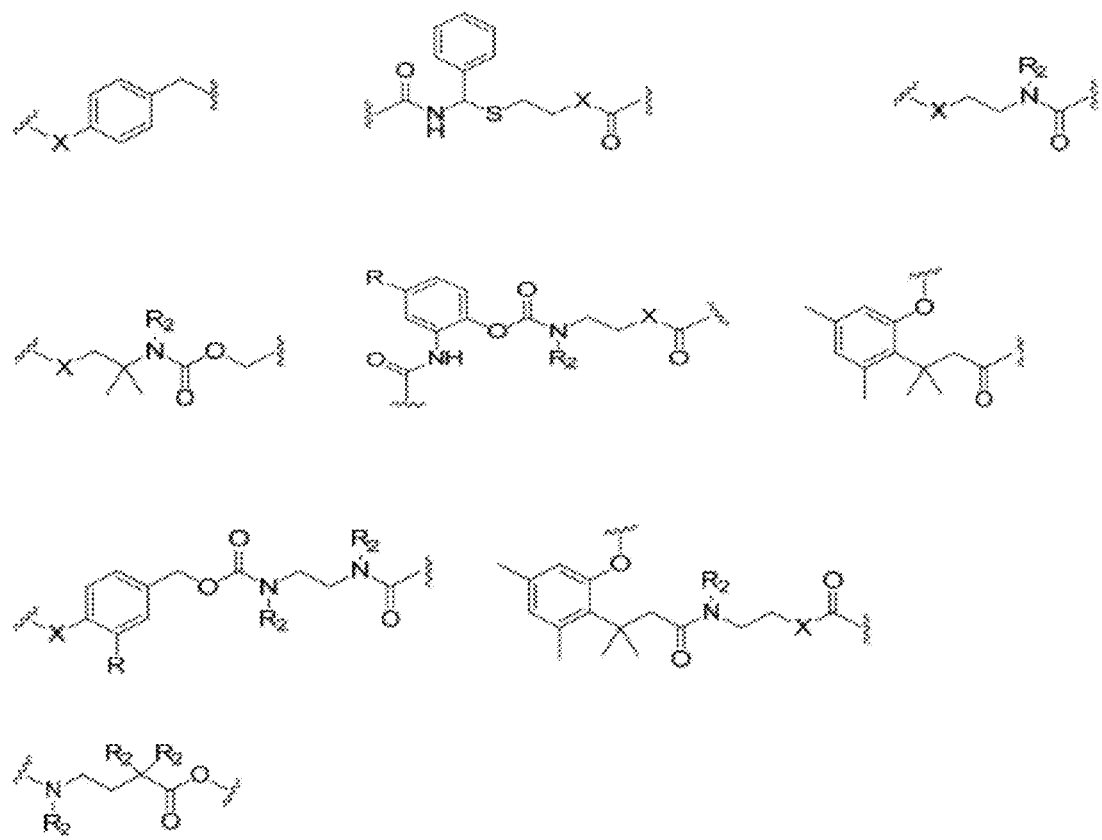
FIG. 3 shows suitable linkers.

The term "linker" refers to a chain of 2 to 50 atoms that link a substrate moiety to the coelenterazine core. Linkers may include one or more heteroatoms. Linkers may also be substituted by oxo groups, amino groups, alkyl groups, halogens and nitro groups. Linkers may also contain aryl groups. Suitable linkers include those shown in FIG. 3, such as a p-aminobenzyl linker. The linkers are suitably "traceless" or "self-immolative" linkers. The term "traceless linker" or "self-immolative linker" refers to a linker wherein cleavage of the substrate moiety from the linker results in spontaneous cleavage of the linker from the coelenterazine core to release coelenterazine. Exemplary "self-immolative linkers" include those shown in FIG. 3.

The term "lower cycloalkyl" refers to a monovalent moiety obtained by removing a hydrogen atom from a hydrocarbon compound having from 3 to 6 carbon atoms. Examples of saturated lower cycloalkyl groups include, but are not limited to, groups such as cyclopropyl, cyclobutyl, cyclopentyl and cyclohexyl. Examples of unsaturated lower cylcoalkyl groups which have one or more carbon-carbon double bonds include, but are not limited to, groups such as cyclopropenyl, cyclobutenyl, cyclopentenyl and cyclohexenyl.

The term "luminescent enzyme" unless specified otherwise, refers to a naturally occurring, recombinant or mutant luminescent enzyme that uses a coelenterazine as a substrate. The luminescent enzyme, if naturally occurring, may be obtained easily by the skilled person from an organism. If the luminescent enzyme is one that occurs naturally or is a recombinant or mutant luminescent enzyme, i.e. one which retains activity in a luciferase-coelenterazine reaction of a naturally occurring luminescent enzyme, it can be obtained readily from a culture of bacteria, yeast, mammalian cells, insect cells, plant cells, or the like, transformed to express a nucleic acid encoding the luminescent enzyme. Further, the recombinant or mutant luminescent enzyme can be derived from an in vitro cell-free system using a nucleic acid encoding the luciferase. Suitable luminescent enzymes include luciferases derived from bioluminescent decapods, such as from the Oplophoroidea, e.g. *Oplophorus*-derived luciferases, marine organisms such as cnidarians (e.g., *Renilla* luciferase), Aristeidae, Solenoceridae, Luciferidae, Sergestidae, Pasipheidae and Thalassocarididae decapoda families, and photoproteins, such as *Aequorin*.

A "luminescent reaction mixture" contains materials that will allow the luminescent enzyme to generate a light signal, i.e., luminescence. The mixture may also contain the enzyme. The materials needed, and the particular concentrations and/or amounts, of the materials needed to generate a luminescent signal will vary depending on the luminescent enzyme used as well as the type of assay being performed. Often other materials will be added to the solution including: a buffer to maintain the reaction at the proper pH, an additive such as PRIONEX or Bovine serum albumin (BSA) to help maintain enzyme activity, reducing agents, detergents, etc.

The term "peptide" refers to a sequence of at least two amino acids. In some embodiments, a peptide may contain no more than 80 amino acids, or no more than 35 amino acids, or no more than 10 amino acids.

The term "saccharide" refers to a sugar or other carbohydrate, especially a simple sugar. It includes both the alpha- and the beta-anomers. The saccharide can be a $C_6$-polyhydroxy compound, typically a $C_6$-pentahydroxy, and often a cyclic glycal. It includes the known simple sugars and their derivatives, as well as polysaccharides with two or more monosaccharide residues. The saccharide can include protecting groups on the hydroxyl groups. The hydroxyl groups of the saccharide can be replaced with one or more acetamido, halo or amino groups. Additionally, one or more of the carbon atoms can be oxidized, for example to keto or carbonyl groups. Suitable saccharides include galactose, glucose, glucoronic acid and neurominic acid.

The term "substituted" is intended to indicate that one or more (e.g., 1, 2, 3, 4, or 5; in some embodiments 1, 2, or 3; and in other embodiments 1 or 2) hydrogens on the group indicated in the expression using "substituted" is replaced with a selection from the indicated group(s), or with a suitable group known to those of skill in the art, provided that the indicated atom's normal valency is not exceeded, and that the substitution results in a stable compound. Suitable substituents include halo, hydroxyl, phenyl, —$NH_2$, —NHMe, —$NMe_2$, —SH, —$CH(OMe)_2$, —$CF_3$, —$OCH_3$, —$SCH_3$, $C_{1-4}$ alkyl, piperazinyl, and piperazinyl substituted with aryl.

Compounds

Coelenterazines are known to luminesce when acted on by a wide variety of bioluminescent proteins, such as marine luciferases. Examples of marine luciferases include *Renilla* luciferase, Aequorin, *Gaussia* luciferase, *Oplophorus* luciferase, and *Cypridina* luciferase.

The invention provides coelenterazine derivatives which are both substrates for a non-luminescent enzyme and pro-substrates for a luminescent protein. Once acted on by the non-luminescent enzyme of interest, the derivative becomes a substrate for a luminescent protein, and thus is detectable by means known to one of ordinary skill in the art.

In some embodiments, the derivatives are compounds of Formulae I-IV shown below:

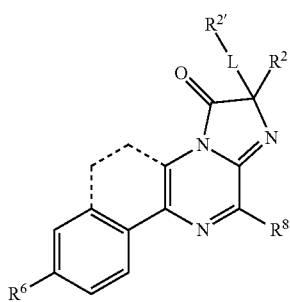
(I)

wherein $R^2$ is —$(CH_2)_n$-T or $C_{1-5}$ alkyl;
$R^{2'}$ is selected from the group consisting of a peptide, an amino acid, a saccharide, —O—$R^A$, —OC(O)O—$R^A$, —$N(R^B)_2$, or —NHC(O)O$R^A$;
$R^6$ is selected from the group consisting of —H, —OH, —$NH_2$—OC(O)R or —$OCH_2OC(O)R$;
$R^8$ is selected from the group consisting of

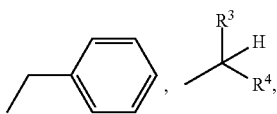

H or lower cycloalkyl;
wherein $R^3$ and $R^4$ are both H or both $C_{1-2}$ alkyl;
$R^A$ is $C_{1-4}$ alkyl, substituted $C_{1-4}$ alkyl, —$CH_2$—$R^C$ or —$CH_2$—V—$R^C$;
each $R^B$ is independently —H or —$R^A$;
$R^C$ is aryl, heteroaryl, substituted aryl or substituted heteroaryl;
L is a linker;
n is 0 to 3;
each R is independently a $C_{1-7}$ alkyl;
T is aryl, heteroaryl, substituted aryl, substituted heteroaryl or cycloalkyl;
V is —S— or —O—; and
the dashed bonds indicate the presence of an optional ring, which may be saturated or unsaturated;

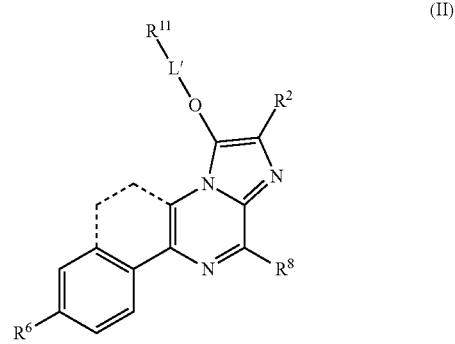
(II)

wherein $R^2$ is —$(CH_2)_n$-T or $C_{1-5}$ alkyl;
$R^6$ is selected from the group consisting of —H, —OH, —$NH_2$, —OC(O)R or —$OCH_2OC(O)R$;
$R^8$ is selected from the group consisting of

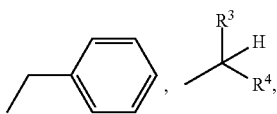

H or lower cycloalkyl;
$R^{11}$ is selected from the group consisting of a peptide, an amino acid, a saccharide, —O—$R^A$, —OC(O)O—$R^A$, —$N(R^B)_2$, or —NHC(O)O$R^A$;
wherein $R^3$ and $R^4$ are both H or both $C_{1-2}$ alkyl;
$R^A$ is $C_{1-4}$ alkyl, substituted $C_{1-4}$ alkyl, —$CH_2$—$R^C$ or —$CH_2$—V—$R^C$;
each $R^B$ is independently —H or —$R^A$;
$R^C$ is aryl, heteroaryl, substituted aryl or substituted heteroaryl;
L' is a direct bond or a linker;
n is 0 to 3;
each R is independently a $C_{1-7}$ alkyl;
T is aryl, heteroaryl, substituted aryl, substituted heteroaryl or cycloalkyl;
V is —S— or —O—; and the dashed bonds indicate the presence of an optional ring, which may be saturated or unsaturated;

(3)

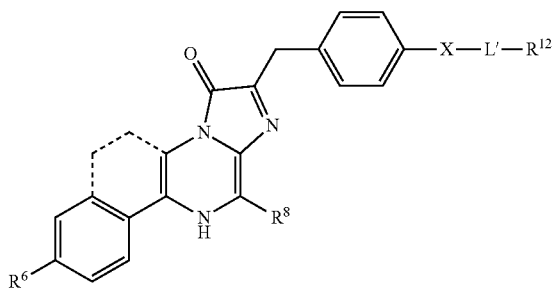

(III)

wherein $R^6$ is selected from the group consisting of —H, —OH, —NH$_2$—OC(O)R or —OCH$_2$OC(O)R;
$R^8$ is selected from the group consisting of

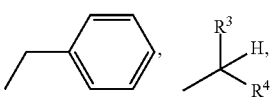

H or lower cycloalkyl;
$R^{12}$ is selected from the group consisting of a peptide, an amino acid, a saccharide, —O—$R^A$, —OC(O)O—$R^A$, —N($R^B$)$_2$, or —NHC(O)O$R^A$;
wherein $R^3$ and $R^4$ are both H or both C$_{1-2}$ alkyl;
$R^A$ is C$_{1-4}$ alkyl, substituted C$_{1-4}$ alkyl, —CH$_2$—$R^C$ or —CH$_2$—V—$R^C$;
each $R^B$ is independently —H or —$R^A$;
$R^C$ is aryl, heteroaryl, substituted aryl or substituted heteroaryl;
L' is a direct bond or a linker;
V is —S— or —O—;
each X is independently —S—, —O— or —NH—;
each R is independently C$_{1-7}$ alkyl; and
the dashed bonds indicate the presence of an optional ring, which may be saturated or unsaturated; or (4)

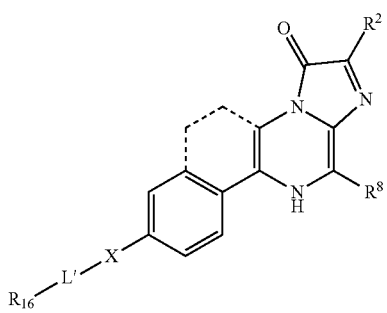

(IV)

wherein $R^2$ is —(CH$_2$)$_n$-T or C$_{1-5}$ alkyl;
$R^8$ is selected from the group consisting of

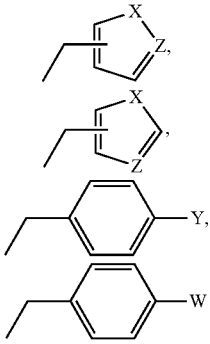

H or lower cycloalkyl;
$R^{16}$ is selected from the group consisting of a peptide, an amino acid, a saccharide, —O—$R^A$, —OC(O)O—$R^A$, —N($R^B$)$_2$, or —NHC(O)O$R^A$.
wherein $R^3$ and $R^4$ are both H or both C$_{1-2}$ alkyl;
$R^A$ is C$_{1-4}$ alkyl, substituted C$_{1-4}$ alkyl, —CH$_2$—$R^C$ or —CH$_2$—V—$R^C$;
each $R^B$ is independently —H or —$R^A$;
$R^C$ is aryl, heteroaryl, substituted aryl or substituted heteroaryl;
L' is a direct bond or a linker;
n is 0 to 3;
T is aryl, heteroaryl, substituted aryl, substituted heteroaryl or cycloalkyl;
V is —S— or —O—;
each X is independently —S—, —O— or —NH—;
each R is independently C$_{1-7}$ alkyl; and
the dashed bonds indicate the presence of an optional ring, which may be saturated or unsaturated.

In some embodiments, $R^2$ is

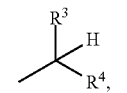

or C$_{2-5}$ alkyl;
each X is independently —S—, —O— or —NH—; Z is —CH— or —N—; Y is —H or —OH; W is —NH$_2$, halo, —OH, —NHC(O)R, —CO$_2$R; and R is C$_{1-7}$ alkyl.

In some embodiments, $R^2$ is and X is O or S. In other embodiments, $R^2$ is C$_{2-5}$ straight-chain alkyl. In certain embodiments, $R^8$ is lower cycloalkyl or H, wherein $R^3$ and $R^4$ are both H or C$_{1-2}$ alkyl. In other embodiments, $R^8$ is benzyl.

In some embodiments, V is S.

Figure 4:
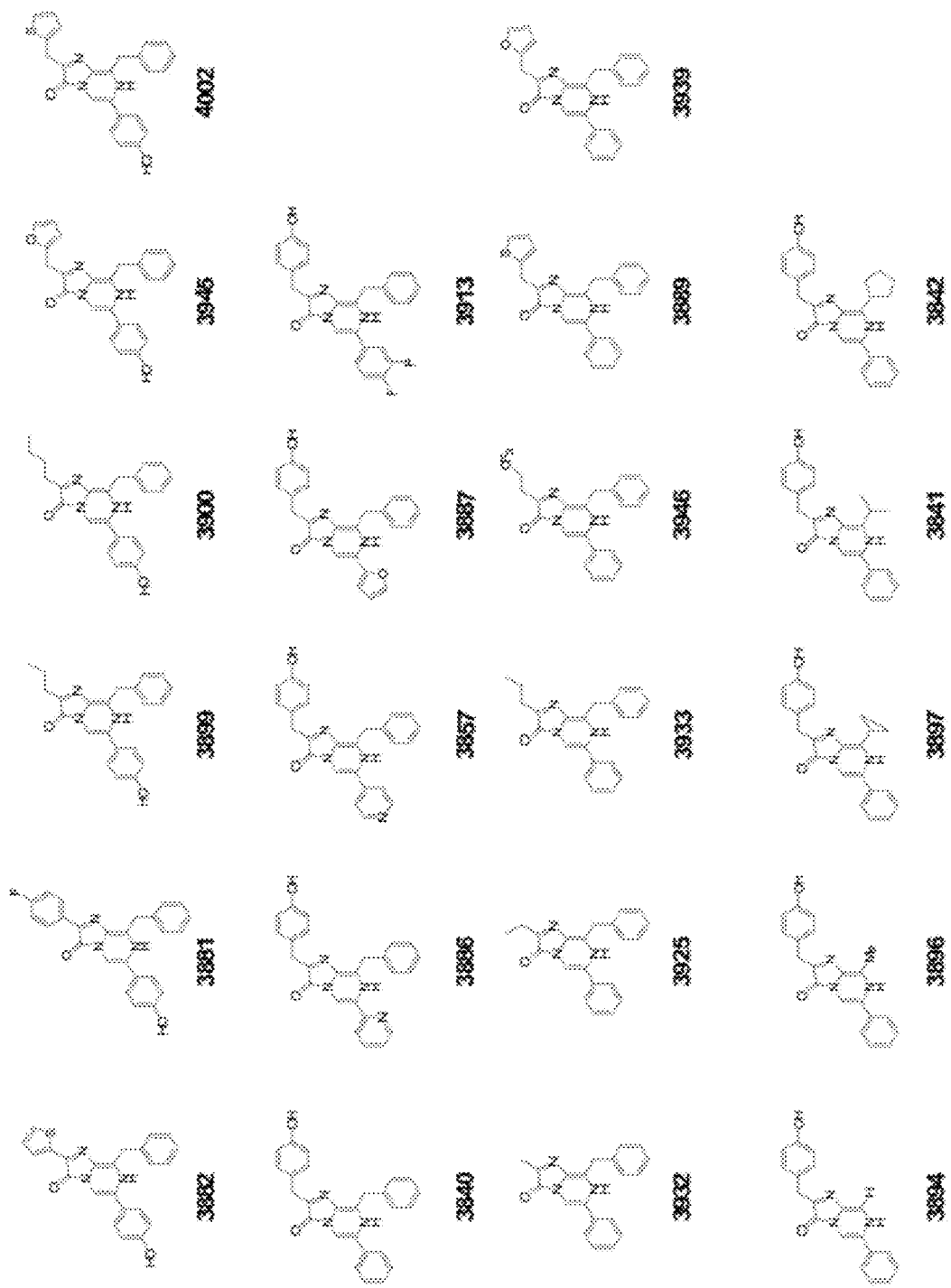
FIG. 4 shows coelenterazines which may be derivatized.

Suitably the compounds of the present invention are derivatives of naturally-occurring ("native") coelenterazines as well as analogs thereof, including coelenterazine-n, coelenterazine-f, coelenterazine-h, coelenterazine-hcp, coelenterazine-cp, coelenterazine-c, coelenterazine-e, coelenterazine-fcp, bis-deoxycoelenterazine ("coelenterazine-hh"), coelenterazine-i, coelenterazine-icp, and 2-methyl coelenterazine, in addition to those disclosed in WO 2003/040100 and U.S. application Ser. No. 12/056,073 (paragraph [0086]), the disclosures of which are incorporated by reference herein. Additional suitable coelenterazines that may be derivatized according to the present invention include those in FIG. 4.

In some embodiments, coelenterazine derivatives of the present invention are substrates for glycosidases. Suitable derivatives include those shown in FIG. 5.

In some embodiments, coelenterazine derivatives of the present invention are substrates for proteases such as caspase 2, caspases 3/7, caspase 6, caspase 8, caspase 9, dipeptidyl peptidase 4 (DPPIV), calpain, chymotrypsin-like proteasome, trypsin-like proteasome, caspase-like proteasome, granzyme B, cathepsins B/L/K, thrombin, trypsin, aminopeptidase, and SARS protease. Suitable peptides and amino acids, and the enzymes for which they are substrates, include those listed in FIG. 6. Additional suitable derivatives include those listed in FIG. 7.

In some embodiments, coelenterazine derivatives of the present invention are substrates for cytochrome P450 enzymes.

In some embodiments, coelenterazine derivatives of the present invention are substrates for diaphorase enzymes.

Methods of Use

The coelenterazine derivatives of the present invention may be used in assay reagents to detect the presence or activity of non-luminescent enzymes such as cytochrome P450 enzymes, proteases or glycosidases. Assays using luminescent enzymes and their substrates are well known in the art. For example, a luminescent enzyme, a luminescent reaction mixture and a coelenterazine derivative that is a substrate of the non-luminescent enzyme may be added to a sample suspected of containing the non-luminescent enzyme. If the non-luminescent enzyme is present in the sample, the non-luminescent enzyme will act on the coelenterazine derivative allowing it to be recognized by the luminescent enzyme to produce a luminescent signal. Alternatively, the non-luminescent enzyme may convert a luminogenic coelenterazine derivative to a non-luminescent form, i.e., in a loss of signal assay.

In some embodiments, the assay may utilize the chemiluminesence of coelenterazines. For example, a coelenterazine derivative that is a substrate of the non-luminescent enzyme may be added to a sample suspected of containing the non-luminescent enzyme. If the non-luminescent enzyme is present in the sample, the non-luminescent enzyme will act on the coelenterazine derivative allowing it to become chemiluminescent and detectable by well-known techniques.

The coelenterazine derivative may be added to the sample prior to or at the same time as the luminescent enzyme. In certain embodiments, the sample may be a cell. Cells may be eukaryotic cells, e.g., yeast, avian, plant, insect or mammalian cells, including but not limited to human, simian, murine, canine, bovine, equine, feline, ovine, caprine or swine cells, or prokaryotic cells, or cells from two or more different organisms, or cell lysates or supernatants thereof. The cells may have been genetically modified via recombinant techniques. In certain aspects, the cell may be in an animal, e.g., transgenic animals, or physiological fluid, e.g., blood, plasma, urine, mucous secretions or the like.

The sample may contain more than one non-luminescent enzyme to be detected. In this case, more than one luminescent enzyme may be used. In addition, more than one substrate may be used. Multiple substrates and/or luminescent enzymes may be used to detect multiple non-luminescent enzymes or other molecule(s) of interest, e.g. test compounds, at the same time, e.g. in a multiplex reaction.

The coelenterazine derivatives are also useful in in situ methods of analyzing cells. Methods of performing in situ analysis of cells using a luciferase are known in the art, see e.g. U.S. Pat. No. 5,998,204. The coelenterazine derivatives are not substrates of the luminescent enzymes prior to exposure to a non-luminescent enzyme. However, upon exposure to the non-luminescent enzyme, the derivatives are converted into compounds that can be readily detected in a light-emitting reaction in the presence of a luminescent enzyme. Thus, it may be determined where the non-luminescent enzyme is located in a cell by in situ imaging. This may be done by contacting a cell expressing a luminescent enzyme with a coelenterazine derivative.

Alternatively, a transgenic animal expressing a gene for a luminescent enzyme can be administered a coelenterazine derivative that is a substrate for a particular non-luminescent enzyme of interest. Imaging technology (e.g. in vivo biophotonic imaging) can then be used to measure luminescence at the site of luminescent enzyme expression in the living, intact animal. Thus, a transgenic animal expressing a luminescent enzyme may be administered a coelenterazine derivative that will be converted into a substrate for the luminescent enzyme in tissues where the appropriate non-luminescent enzyme of interest is expressed. If the luminescent enzyme is also expressed in that tissue, a luminescent signal will be produced and can be detected by any suitable means. Thus, test compounds, e.g. drugs, can be tested in an animal-based assay. The test compound should be administered to the animal prior to the coelenterazine derivative. Alternatively, tissue from transgenic animals can be used in tissue based assay.

In some embodiments, a non-transgenic animal may be administered a coelenterazine derivative that is a substrate for a particular non-luminescent enzyme of interest. The derivative will be converted into a substrate for a luminescent enzyme in tissues where the appropriate non-luminescent enzyme is expressed. A biological sample, e.g., blood, serum, bile, urine, feces, or tissue, can be obtained from the animal and contacted with a luminescent enzyme. The resulting signal can be detectable by any suitable means. Thus, test compounds, e.g. drugs, can be tested in an animal-based assay. The test compound should be administered to the animal prior to the coelenterazine derivative.

In some embodiments, test compounds such as candidate drugs can be screened and evaluated for their activities as, e.g., (1) substrates of a non-luciferase enzyme, (2) regulators, e.g. inhibitors, inducers or activators, of a non-luciferase enzyme, or (3) modifiers of a cellular condition (e.g., viability, increasing reactive oxygen species, or increasing reducing potential). The coelenterazine derivatives may also be used to distinguish between substrates and inhibitors of a non-luciferase enzyme. The screening may be performed either in vitro or in vivo.

In addition, for any of the bioluminogenic assays described herein, other reagents may be added to reaction mixtures, including but not limited to those that inhibit or prevent inactivation of luciferase, or otherwise extend or enhance luminescent signal.

Kits

The invention also provides kits for determining the presence or activity of one or more non-luciferase enzymes. The kit may include one or more of the following: coelenterazine derivative(s), non-luciferase enzyme(s), coelenterazine-dependent luminescent enzyme(s), and reaction buffer(s). The reaction buffers may be present in individual formulations for the non-luciferase enzyme reactions and the luminescent enzyme reactions or in a single formulation for a single step assay. The kits of the present invention may also contain inhibitors, activators and/or enhancers for the non-luciferase enzyme(s). The kits of the present invention may also contain a positive and/or negative control for the assay.

The invention is further described by the following non-limiting examples.

EXAMPLES

Example 1

Synthesis of z-DEVD-coelenterazine-h (compound 21)

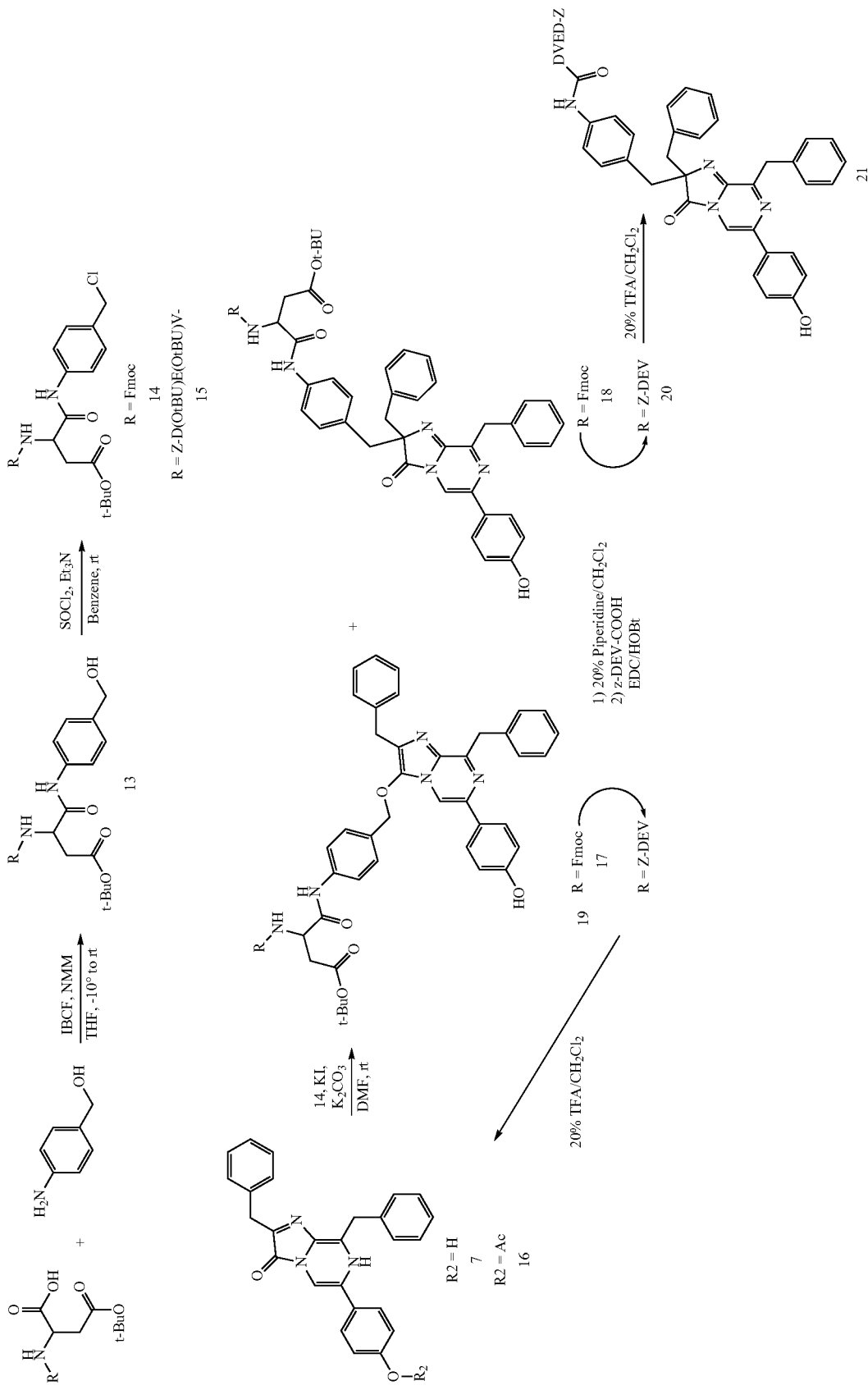

tert-Butyl 3-((((9H-fluoren-9-yl)methoxy)carbonyl)amino)-4-((4-(hydroxymethyl)phenyl)amino)-4-oxobutanoate (13): A flask was charged with Fmoc-Asp(OtBu)-OH (6.7 g, 16.28 mmol) and 100 ml of dry THF. To this solution, at ambient temperature, neat N-methylmorpholine (1.9 mL, 17.28 mmol) was added, and the solution was cooled to −20° C. The neat isobutylchloroformate (2.2 mL, 16.96 mmol) was added via syringe and the resulting suspension was stirred for 10 minutes. The amino alcohol (2.0 g, 16.24 mmol) was added in one portion, and the reaction mixture was stirred for 10 minutes before the cold bath was removed and stirring continued for 2 hours at ambient temperature. The reaction mixture was diluted with 300 mL of ethyl acetate, and the mixture was washed sequentially with two 50 mL portions of water, 50 mL of 0.5 M HCl and two 50 mL portions of brine solution. The organic phase was dried ($MgSO_4$) and concentrated under vacuum. The residue was chromatographed over silica using a heptane/ethyl acetate gradient. This gave 5.2 g (10.7 mmol) of the product as a white solid. $^1H$ NMR (300 MHz, dmso) d 10.02 (s, 1H), 7.89 (d, J=7.5, 2H), 7.81-7.67 (m, 3H), 7.55 (d, J=8.4, 2H), 7.47-7.27 (m, 4H), 7.24 (d, J=8.4, 2H), 5.09 (t, J=5.7, 1H), 4.51 (m, 1H), 4.43 (d, J=5.7, 2H), 4.37-4.16 (m, 3H), 2.76-2.51 (m, 2H), 1.37 (s, 9H).

tert-Butyl 3-((((9H-fluoren-9-yl)methoxy)carbonyl)amino)-4-((4-(chloromethyl)phenyl)amino)-4-oxobutanoate (14): A flask was charged with alcohol (13) (0.5 g, 0.97 mmol) and 15 mL of dry benzene. To this suspension, at ambient temperature, neat triethylamine was added, and, after stirring for 2 minutes, the mixture was cooled in an ice/water bath for 10 minutes. To this, neat thionyl chloride (78 µL, 1.07 mmol) was added, and, after 2 minutes, the cold bath was removed and stirring continued at ambient temperature for 3 hours. The reaction mixture was filtered through a pad of celite, and the filter cake was rinsed with 30 mL of dry benzene. The filtrate was concentrated under vacuum, and the residue was purified by column chromatography over silica using methylene chloride. This gave 457 mg (0.85 mmol) of the product as a sticky white solid. $^1H$ NMR (300 MHz, dmso) δ 10.16 (s, 1H), 7.89 (d, J=7.5, 2H), 7.79 (d, J=8.1, 1H), 7.76-7.68 (m, 2H), 7.61 (d, J=8.5, 2H), 7.44-7.27 (m, 6H), 4.72 (s, 2H), 4.58-4.44 (m, 1H), 4.33-4.18 (m, 3H), 2.63 (ddd, J=6.0, 14.6, 21.8, 2H), 1.37 (s, 9H).

Compounds 17 and 18: A dry flask was charged with coelenterazine-h (7) (200 mg, 0.37 mmol) and 15 mL of anhydrous, deoxygenated DMF under an argon atmosphere. To this solution, at ambient temperature, potassium iodide (31 mg, 0.19 mmol) and potassium carbonate (51 mg, 0.37 mmol) were added, and the mixture was stirred for about 2 minutes. To this, compound 14 was added, and the mixture was stirred for 18 hours. The products were purified by both reverse and normal phase chromatography.

Compounds 19 and 20: To a solution of either compound 17 or 18 (365 mg, 0.4 mmol) in 3 mL of dichloromethane at ambient temperature, a solution of piperidine (2 mL) in 7 mL of dichloromethane was added. The reaction mixture was stirred for 30 minutes, diluted with 50 mL of toluene and concentrated under vacuum. The residue was purified by reverse phase chromatography using a gradient of 0.1% TFA/water to acetonitrile. The mixture of regioisomers (133 mg, 0.19 mmol) was dissolved in 2 mL of dry DMF, and HOBt (30 mg, 0.22 mmol) and z-DEVD-$CO_2$H (140 mg, 0.23 mmol) was added. To this solution, at ambient temperature, EDC (42 mg, 0.22 mmol) was added, and the reaction mixture was stirred overnight. The crude reaction mixture was diluted with 1 mL of acetonitrile and purified by reversed phase column chromatography using a gradient of 20 mM ammonium acetate to acetonitrile. This gave 54 mg of compound 19 and 69 mg of compound 20.

Compound 21: A crude mixture of compounds 19 and 20 were dissolved in 2 mL of dichloromethane, and, to this solution at ambient temperature, a deprotection cocktail comprised of 4 mL trifluoroacetic acid, 2 mL of dichloromethane, 0.4 mL of triisopropylsilane and 0.4 mL of thioanisole was added. The reaction mixture was stirred for 3 hours and diluted with 30 mL of diethyl ether. The suspension was centrifuged, and the solid was triturated twice with 10 mL portions of diethyl ether. The residue was dissolved in 2 mL of methanol and purified by reverse phase chromatography using a gradient of 20 mM ammonium acetate to acetonitrile. This gave 9 mg of compound 21 as an orange solid.

Example 2

Biological Testing of z-DEVD-coelenterazine-h (Compound 21)

Compound 21 (50 µM) was combined with *Renilla* luciferase (6.5 µg/ml, *Renilla*-GST fusion) in 50 mM HEPES buffer pH 7.2, 2 mM DTT, and 0.5% CHAPS and incubated for 20 minutes to remove any free coelenterazine derivatives that may be substrates for *Renilla* luciferase. Purified caspase-3 enzyme (50 U/ml) or buffer control was added in a 1:1 volume ratio for final concentrations of 25 µM Z-DEVD-coelenterazine h derivative substrate, 25 U/ml caspase-3 and 3.25 ug/ml luciferase. Luminescence was measured over 110 minutes. Over time, a one hundred-fold increase in luminescence was seen relative to control samples that did not contain caspase, indicating enzymatic release of coelenterazine and validating that the coelenterazine compounds of the present invention can be used to detect caspase enzymes (FIG. 1).

Example 3

Alternative Synthesis of z-DEVD-coelenterazine-h (Compound 21)

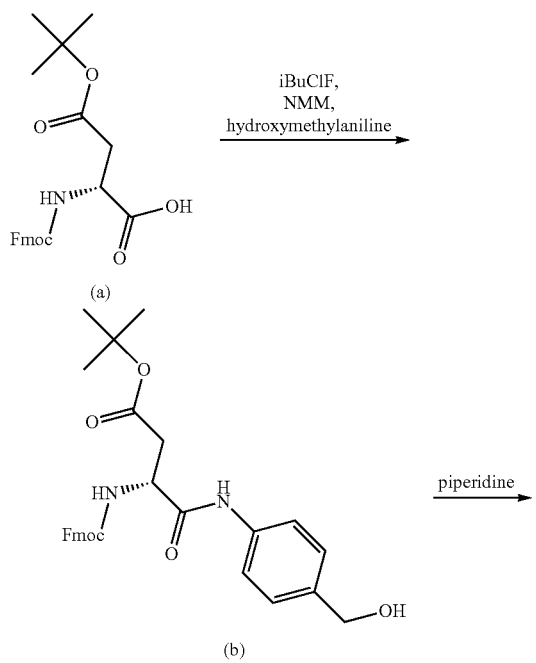

-continued

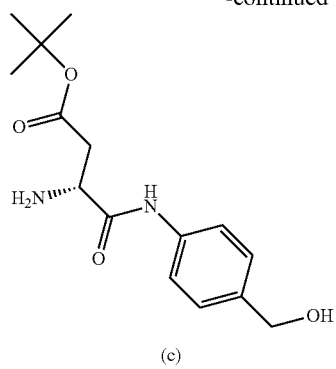

(c)

Z-D(tBu)E(tBu)V-COOH
EDAC, HOBt, DMF
→

-continued

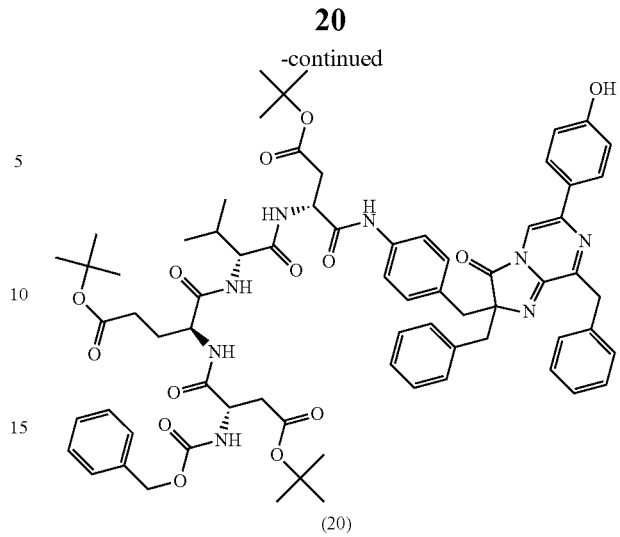

(20)

(R)-tert-butyl 3-amino-4-(4-(hydroxymethyl)phenylamino)-4-oxobutanoate (c). In a 250 mL round bottom flask, b (6 g, 0.011 mole) was dissolved in dimethyl formamide (60 mL). Piperidine (10 mL) was added. After 4 hours, TLC showed reaction completion. Solvent was evaporated. Residue was purified by loading on Celite (15 g in 250 mL EtOAc) and eluting over silica (80 g) with DCM ramping to MeOH (10% in DCM). Combined factions were evaporated. Yield (76%); Rf=0.2 (50/50 Hept/EtOAc), $^1$H NMR (300 MHz, dmso) δ 7.56 (d, J=8.3, 2H), 7.22 (d, J=8.3, 2H), 5.06 (t, J=5.4, 1H), 4.41 (d, J=4.6, 2H), 3.61 (t, J=6.5, 1H), 2.59 (dd, J=5.8, 15.5, 1H), 2.41 (dd, J=7.2, 15.6, 1H), 1.35 (s, 9H); m/z.

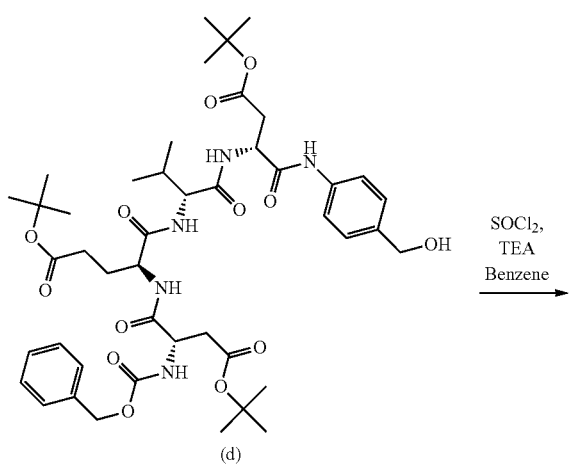

(d)

SOCl$_2$,
TEA
Benzene
→

(5S,8S,11R,14R)-tert-butyl 5-(2-tert-butoxy-2-oxoethyl)-8-(3-tert-butoxy-3-oxopropyl)-14-(4-(hydroxymethyl)phenylcarbamoyl)-11-isopropyl-3,6,9,12-tetraoxo-1-phenyl-2-oxa-4,7,10,13-tetraazahexadecan-16-oate (d). To a 100 mL round bottom flask, Z-D(tBu)E(tBu)V—OH (3.96 g, 6.5 mmol), c (1.6 g, 5.4 mmol), HOBt (0.915 g, 5.9 mmol), and DMF (25 mL) were added. To the stirring solution, EDAC (1.15 g, 5.9 mmol) was added. After 18 hours, the solvent was evaporated, and the residue redissolved in EtOAc (200 mL). The solution was washed with citric acid (30%-50 mL), bicarbonate$_{sat}$ (50 mL), water (2×50 mL) and brine (50 mL). The material was adsorbed on Celite (15 g) and purified over silica ramping from heptane to EtOAc. Yield (74%). $^1$H NMR (300 MHz, dmso) δ 9.85 (s, 1H), 8.33 (d, J=7.7, 1H), 7.95 (d, J=8.1, 1H), 7.83 (d, J=8.3, 1H), 7.59 (d, J=8.3, 1H), 7.53 (d, J=8.5, 2H), 7.43-7.26 (m, 5H), 7.21 (d, J=8.6, 2H), 5.06 (t, J=5.7, 1H(disappears on D$_2$O shake)), 5.02 (d, J=4.7, 2H), 4.70 (q, J=7.7, 1H), 4.41 (d, J=5.6, 2H(collapses to s on D$_2$O shake)), 4.38-4.25 (m, 2H), 4.17-4.09 (m, 1H), 2.79-2.63 (m, 1H), 2.62-2.35 (m, 4H), 2.26-2.11 (m, 2H), 2.00-1.79 (m, 2H), 1.73 (d, J=6.0, 1H), 1.34 (dd, J=4.7, 7.4, 31H), 0.81 (t, J=6.3, 6H). MS: Calcd for C$_{45}$H$_{65}$N$_5$O$_{13}$ 883.5; found 883.7.

(5S,8S,11R,14R)-tert-butyl 5-(2-tert-butoxy-2-oxoethyl)-8-(3-tert-butoxy-3-oxopropyl)-14-(4-(chloromethyl)phenylcarbamoyl)-11-isopropyl-3,6,9,12-tetraoxo-1-phenyl-2-oxa-4,7,10,13-tetraazahexadecan-16-oate (e). To a 100 mL RB flask, d (3.56 g, 4 mmol) with benzene (50 mL) was added. The solution was evaporated and stored overnight under high vacuum. Dry benzene (70 mL) was added to the solid along with TEA (610 μL, 4.4 mmol). The solution was chilled in an ice bath, and SOCl$_2$ (320 μL, 4.4 mmol) was added slowly. The solution was allowed to warm to room

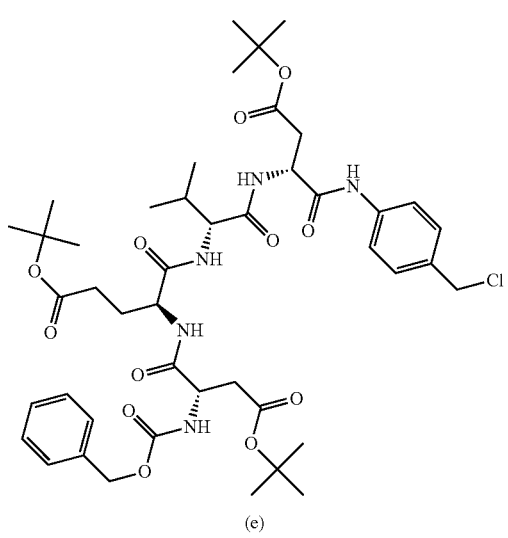

(e)

Coel-h
K$_2$CO$_3$
DMF
↓ temperature. After 4 hours, additional TEA (241 µL) and SOCl$_2$ (100 µL) was added. After additional 2 hours, the reaction mixture was adsorbed onto Celite (10 g) and eluted over silica ramping from DCM to 5% MeOH in DCM. Yield (33%). $^1$H NMR (300 MHz, dmso) δ 10.00 (s, 1H), 8.35 (d, J=7.8, 1H), 7.95 (d, J=7.8, 1H), 7.84 (d, J=8.3, 1H), 7.67 (d, J=8.6, 3H), 7.41-7.22 (m, 7H), 5.11-4.91 (m, 2H), 4.77-4.59 (m, 3H), 4.43-4.21 (m, 2H), 4.19-4.04 (m, 1H), 3.30 (s, (water)), 2.79-2.32 (m, 4H+DMSO), 2.26-2.07 (m, 2H), 2.00-1.79 (m, 2H), 1.77-1.60 (m, 1H), 1.40-1.24 (m, 27H), 0.81 (t, J=6.4, 6H).

(5S,8S,11R,14R)-tert-butyl 5-(2-tert-butoxy-2-oxoethyl)-8-(3-tert-butoxy-3-oxopropyl)-14-(4-((2,8-dibenzyl-6-(4-hydroxyphenyl)imidazo[1,2-a]pyrazin-3-yloxy)methyl)phenylcarbamoyl)-11-isopropyl-3,6,9,12-tetraoxo-1-phenyl-2-oxa-4,7,10,13-tetraazahexadecan-16-oate (20). To an argon degassed vial containing coelenterazine-h (50 mg, 122 µmol) and K$_2$CO$_3$ (34 mg, 245 µmol), a degassed solution of e (133 mg, 147 µmol) in DMF (500 µL) was added. After 2 hours, the reaction was injected directly on RP-HPLC and eluted with a ramp of 0.1% TFA (aq) to acetonitrile. The major peak was isolated and evaporated. Yield (13%). UV: peaks 250, 300, and 420 nm. $^1$H NMR (300 MHz, dmso) δ 9.79 (s, 1H), 8.27 (d, J=7.5, 1H), 7.92 (d, J=8.0, 1H), 7.85 (d, J=10.1, 1H), 7.58 (d, J=8.3, 1H), 7.53 (d, J=8.7, 2H), 7.45-7.14 (m, 15H), 7.09-6.80 (m, 6H), 6.72 (d, J=8.8, 2H), 5.13-4.90 (m, 2H), 4.73-4.53 (m, 1H), 4.22 (dd, J=5.0, 17.7, 3H), 4.16-4.01 (m, 3H(2H after D$_2$O shake)), 3.25-3.01 (m, J=10.0, 16.5, 4H), 2.76-2.53 (m, J=15.6, 2H), 2.51-2.33 (m, 2H+DMSO), 2.24-2.04 (m, 2H), 1.99-1.77 (m, 2H), 1.76-1.61 (m, 1H), 1.40-1.07 (m, 27H), 0.89-0.62 (m, 6H). MS: Calcd for C71H84N8O14 1272.6; found 1272.8.

Example 4

Synthesis of 30

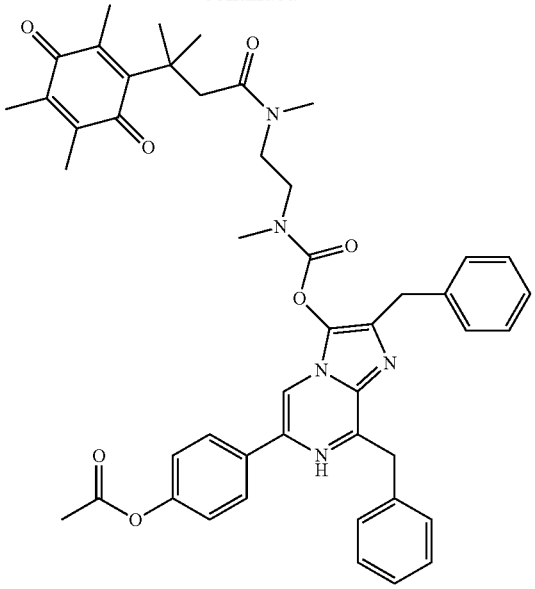

A mixture of coelenterazine acetyl ester (0.50 g, 1.14 mmol), quinone trimethyllock C2-diamine carbonyl chloride (0.436 g, 1.14 mmol), DMAP (0.139 g, 1.14 mmol) and TEA (0.115 g, 1.14 mmol) in 20 ml of methylene dichloride was stirred overnight at room temperature. The compound was purified by silica chromatography using heptane/ethyl acetate as an eluent to give a yield of 20% (0.184 g). $^1$H NMR (300 MHz, CD$_2$Cl$_2$) δ 8.47 (s, 1H), 8.04 (d, 2H), 7.55 (d, 2H), 7.0-7.5 (m, 9H), 4.57 (s, 2H, CH2), 4.16 (s, 2H, CH2), 3.2-3.7 (m, 4H, NCH2), 2.7-3.2 (m, 8H, 2NCH3+CH2), 2.30 (s, 3H, CH3), 1.0-2.2 (m, 15 H, CH3). MS (m/e): 796.5 (M+).

Example 5

Synthesis of 40

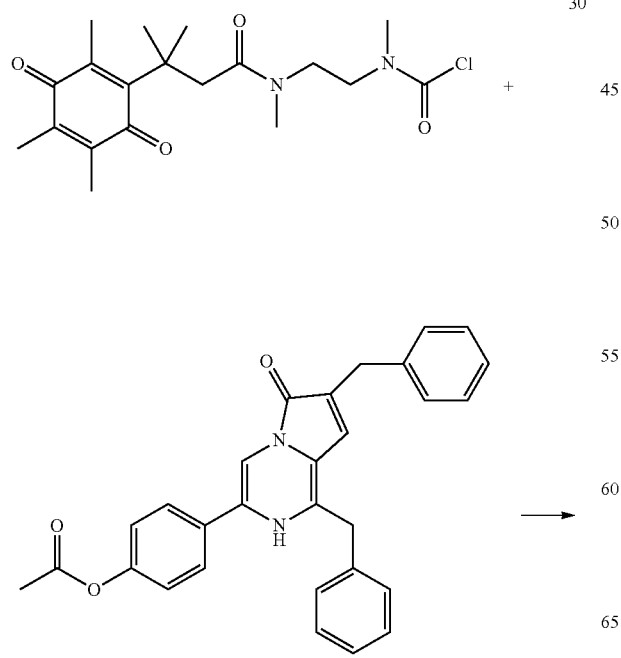

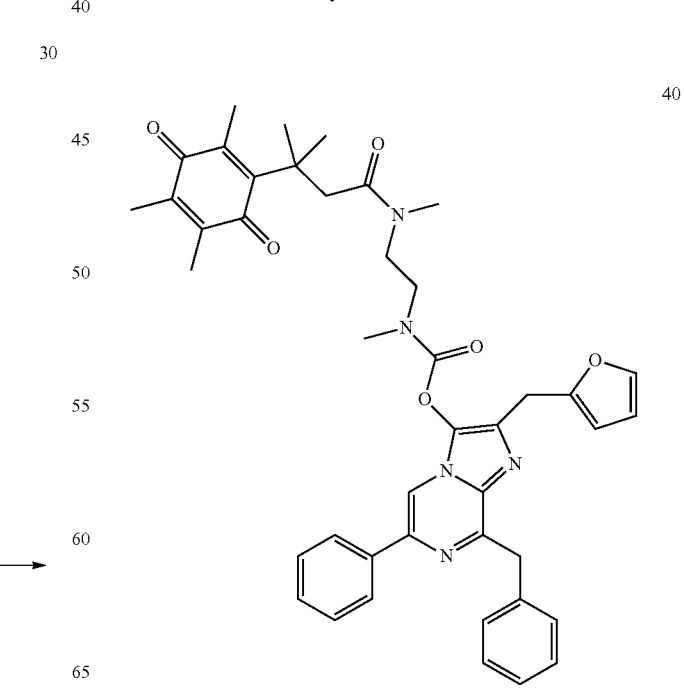

40 was made by employing the similar method for preparing 30 (Example 4). The compound was purified by silica chromatography using heptane/ethyl acetate as an eluent to give a yield of 60% (0.32 g). $^1$H NMR (300 MHz, CD2Cl2) δ 8.47 (s, 1H), 8.03 (m, 2H), 7.57 (d, 2H), 7.1-7.5 (m, 7H), 6.33 (s, 1H), 6.17 (s, 1H), 4.58 (s, 2H, CH2), 4.19 (s, 2H, CH2), 3.3-3.7 (m, 4H, NCH2), 2.7-3.2 (m, 8H, 2NCH3+CH2), 1.0-2.2 (m, 15 H, CH3). MS (m/e): 728.5 (M+). HPLC purity: 90% at 262 nm.

Example 6

Synthesis of 50

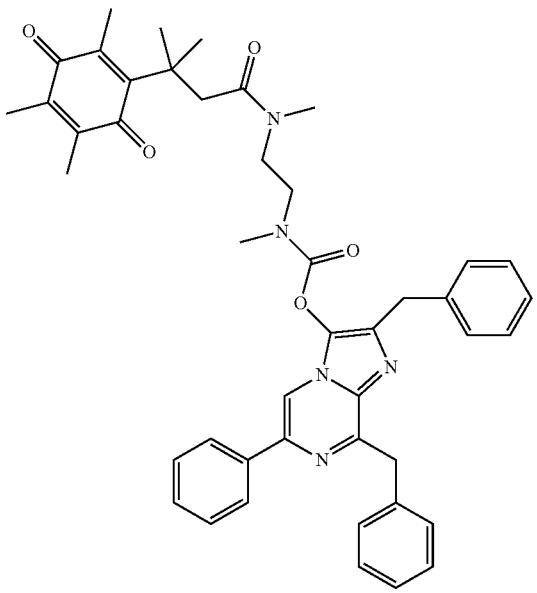

50

50 was made by employing the similar method for preparing PBI 4442 (Example 20). The compound was purified by silica chromatography using heptane/ethyl acetate as an eluent to give a yield of 17% (0.15 g). $^1$H NMR (300 MHz, CD$_2$Cl$_2$) δ 8.42 (s, 1H), 7.99 (m, 2H), 7.57 (d, 2H), 7.1-7.5 (m, 10H), 4.58 (s, 2H, CH2), 4.19 (s, 2H, CH2), 3.3-3.7 (m, 4H, NCH2), 2.7-3.2 (m, 8H, 2NCH3+CH2), 1.0-2.2 (m, 15 H, CH3). MS (m/e): 738.5 (M+). HPLC purity: 95% at 262 nm.

Example 7

Measuring Metabolically Active Cells Using Quinone Derivatives

This example demonstrates the use of quinine-containing coelenterazine derivatives to measure the amount of metabolically active cells. Viable cells maintain a metabolically active state that is inevitably lost when cells are damaged. Upon entering the living cells, the quinone coelenterazine is reduced to a coelenterazine derivative that is a substrate for a coelenterazine-utilizing luciferase, e.g., *Oplophorus* or *Renilla* luciferase. Conversion of the quinone coelenterazine is proportional to the number of metabolically active cells, and therefore can be measured quantitatively by monitoring light produced by luciferase reaction.

Figure 8:
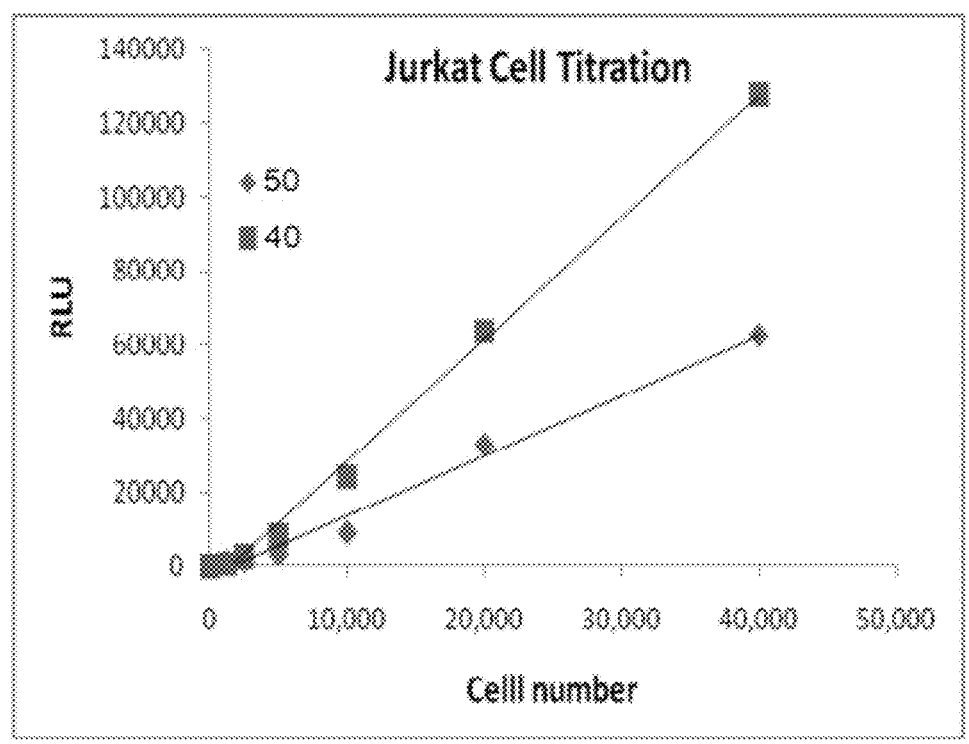
FIG. 8 shows a linear correlation between cell number and luminescence indicating a direct relationship between luminescence measured with compounds 40 and 50 and cell number.

Two-fold serial dilutions of Jurkat cells were prepared in PBS, and 50 μl per well transferred to wells in 96-well plates. Compounds 40 and 50 were diluted in PBS to make 50 μM and 100 μM stocks, respectively. 10 μl of prepared compound stocks were added to the cells, and the cells were placed into 37° C., 5% CO$_2$ incubator. Following 30 minutes incubation, the cells were removed from incubator, cooled at room temperature for 10 minutes, and 50 μl of *Oplophorus* luciferase detection reagent added directly to the wells. The samples were mixed, incubated at room temperature for 20 minutes, and luminescence measured. FIG. 8 shows the linear correlation between cell number and luminescence indicating a direct relationship between luminescence and cell number.

Example 8

Caspase 3 Assay Using an Oplophorus Luciferase and Compound 21

Figure 2:
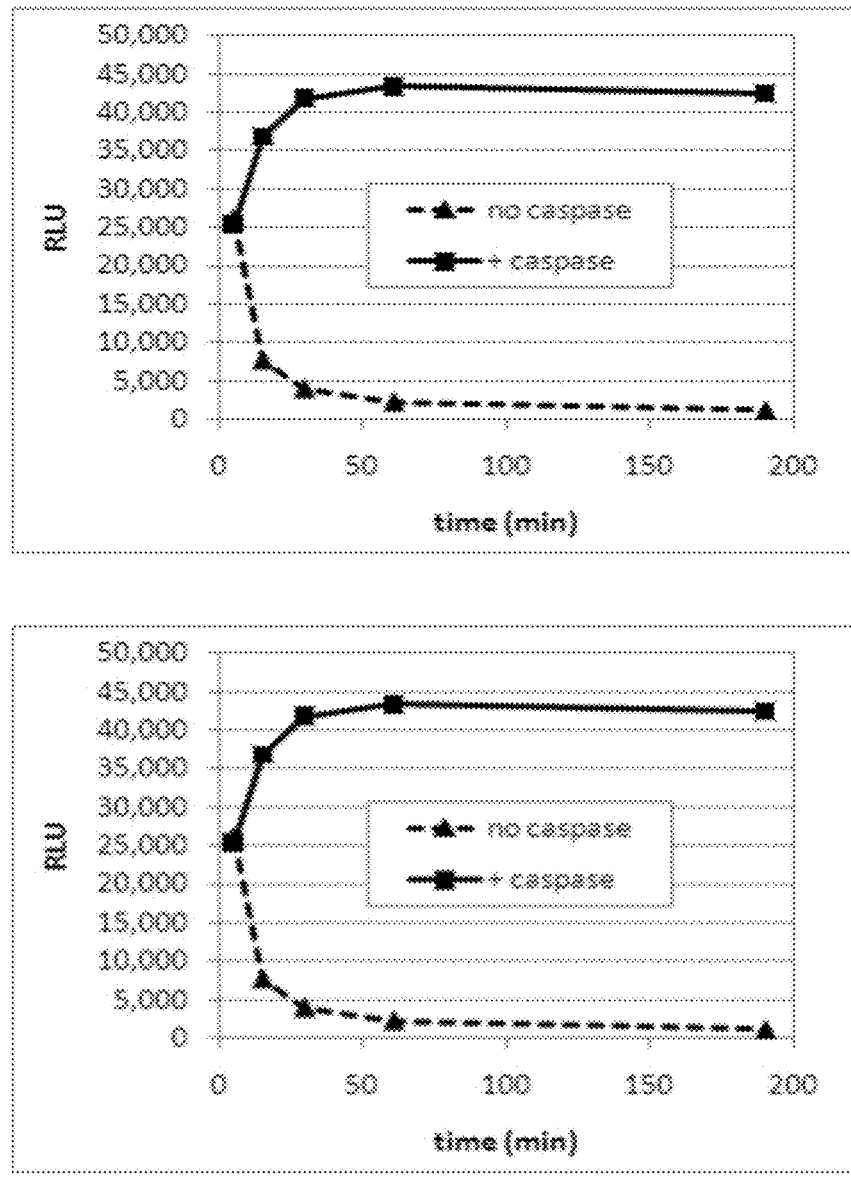
FIG. 2 shows the results of a caspase 3 assay using an *Oplophorus*-derived luciferase and z-DEVD-coelenterazine-h.

An *Oplophorus* luciferase (OgLuc) variant, 9B8 opt, was used in a bioluminescent assay using a pro-coelenterazine substrate comprising the DEVD caspase-3 cleavage sequence. Purified caspase-3 enzyme was mixed with an *E. coli* lysate sample expressing the variant 9B8 opt, which was purified using the HALOLINK™ Resin (Promega Corp.) according to manufacturer's instructions, and diluted 10-fold in a buffer containing 100 mM MES pH 6.0, 1 mM CDTA, 150 mM KCl, 35 mM thiourea, 2 mM DTT, 0.25% TERGITOL® NP-9 (v/v), 0.025% MAZU®, with or without 23.5 μM z-DEVD-coelenterazine-h in 100 mM HEPES pH 7.5. The caspase-3 enzyme was incubated with the lysate sample for 3 hrs at room temperature, and luminescence detected on a Turner MODULUS™ luminometer at various time points. A sample containing only bacterial lysate and a sample containing only caspase-3 were used as controls. Three replicates were used. FIG. 2 and Table 1 demonstrate that the pro-coelenterazine substrates of the present invention can be used to detect an enzyme of interest.

TABLE 1

| | +/− caspase | |
|---|---|---|
| time (min) | −<br>RLU | +<br>RLU |
| 5.0 | 26,023 | 25,411 |
| 15.3 | 7,707 | 36,906 |
| 29.9 | 4,013 | 41,854 |
| 60.9 | 2,305 | 43,370 |
| 190.3 | 1,155 | 42,448 |

Another *Oplophorus* luciferase variant, L27V02 ("L27V"), was used in a bioluminescent assay using a pro-coelenterazine substrate comprising the DEVD caspase-3 cleavage sequence. Purified caspase-3 enzyme (1 mg/mL) in 100 mM MES pH 6 (50 μL) was mixed with 227 nM of the L27V02 variant and 47 μM PBI-3741 (z-DEVD-coelenterazine-h) in 50 μL assay buffer (100 mM MES pH 6, 35 mM Thiourea, 0.5% TERGITOL® NP-9 (v/v), 1 mM CDTA, 2 mM DTT and 150 mM KCl). Reactions were incubated for 3 hrs at room temperature, and luminescence detected as previously described. The assay with the L27V02 variant was compared to a firefly luciferase version of the assay, Caspase 3/7 Glo (Caspase-Glo; Promega Corp.). Table 2 demonstrates that the compounds of the present invention can be used in a bioluminescent assay to detect an enzyme of interest.

TABLE 2

|  | (+) caspase | +/− | (−) caspase | +/− |
|---|---|---|---|---|
| L27V | 11,532 | 93 | 803 | 25 |
| Caspase-Glo | 15,156,567 | 793,981 | 302 | 5 |

Prophetic Example 9

Synthesis of O-(8-benzyl-2-(furan-2-ylmethyl)-6-phenylimidazo[1,2-a]pyrazin-3(7H)-on-yl) galactoside (25)

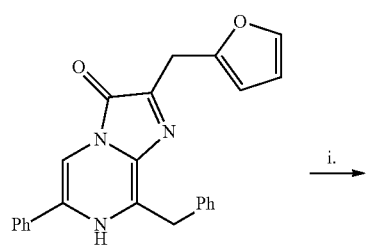

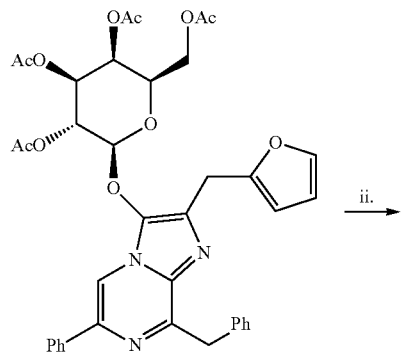

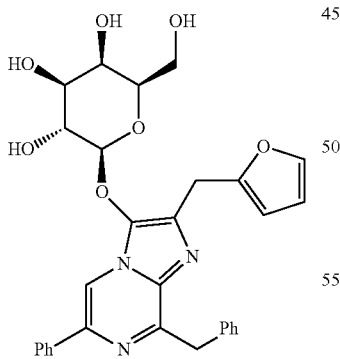

i. acetobromo alpha-D-galactose, AgOTf, TMU, DCM. ii. KOMe, THF

Typical synthesis of typical beta sugar pro-coelenterazine. (O-(8-benzyl-2-(furan-2-ylmethyl)-6-phenylimidazo[1,2-a]pyrazin-3(7H)-on-yl) 3,4,5,6-tetraacetoxy-beta-galactoside)

To a 100 mL round bottom flask, the appropriate acetobromo-alpha sugar (e.g. acetobromo alpha-D-galactose) (1.1EQ), appropriate coelenterazine (e.g. (8-benzyl-2-(furan-2-ylmethyl)-6-phenylimidazo[1,2-a]pyrazin-3(7H)-one) (1.0 EQ, 100 mg), and silvertriflate (67 mg, 1EQ) is added and is degassed with argon for 30 minutes. 2 mL dichloromethane and 70 μL of tetramethylurea is injected and is stirred at room temperature for 3 hours. 4 mL Acetonitrile is added, and the solids are filtered. The sample is purified by injecting the supernatant on preparative 250× 41 mm C18 RP-HPLC column and the appropriate fractions are collected by eluting with a gradient of water to acetonitrile or other appropriate solvent. The fractions can be evaporated to yield compound.

To the sample above, 1 mL methanol is added and cooled to 0° C. in ice bath. A solution of potassium methoxide (5.2 EQ) in methanol or THF can then be added. After 30 min, exactly 5.2 equivalents of acetic acid is added. 3 mL acetonitrile can then be added, and the sample can be filtered. The sample can be purified by injecting the supernatant on preparative 250×41 mm C18 RP-HPLC column, and the appropriate fractions can be collected by eluting with a gradient of water to acetonitrile or other appropriate solvent. The fractions can be evaporated to yield compound (25).

Prophetic Example 10

Synthesis of Various P450 Substrates

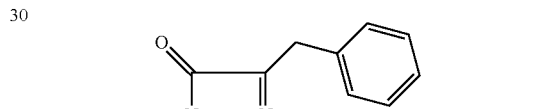

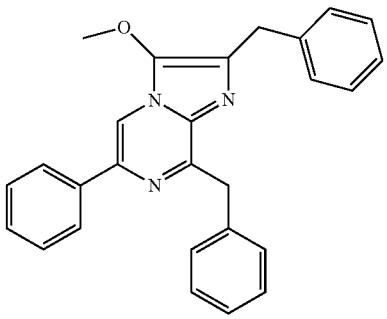

1

To a mixture of the coelenterazine and 1.1 equivalents of potassium carbonate in DMF, under an argon atmosphere, could be added one equivalent of methyl iodide at room temperature. Reaction progress can be monitored by thin layer chromatography. Upon completion of the reaction, the mixture can be cooled in an ice bath for several minutes and a volume of water equal to the reaction volume can be added. The resulting mixture can be extracted with a suitable organic solvent (e.g. ethyl acetate), and the extracts can be concentrated to give the crude compound 1. The material may be further purified by chromatography over silica gel.

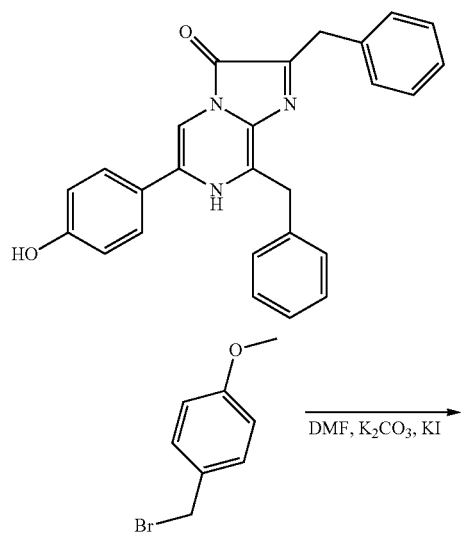

1

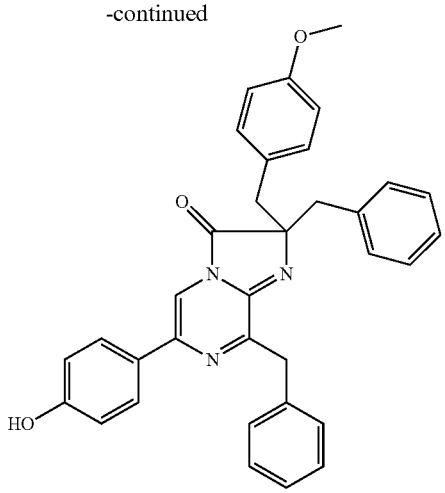

2

To a mixture of the coelenterazine and 1.1 equivalents of both potassium carbonate and potassium iodide, in DMF under an argon atmosphere, one equivalent of p-methoxy-benzyl bromide at room temperature could be added. Reaction progress can be monitored by thin layer chromatography, and upon completion, the reaction mixture can be cooled in an ice bath for several minutes before addition of a volume of water equal to the reaction volume. The resulting mixture can be extracted with a suitable organic solvent (e.g. ethyl acetate), and the extracts can be concentrated to give the crude compound 2. The material may be further purified by chromatography over silica gel.

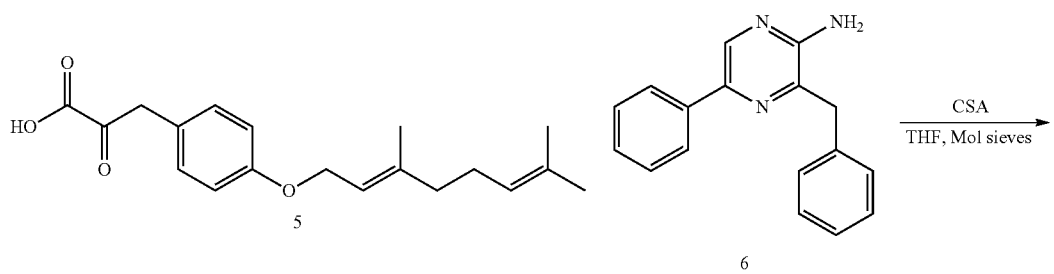

5

6

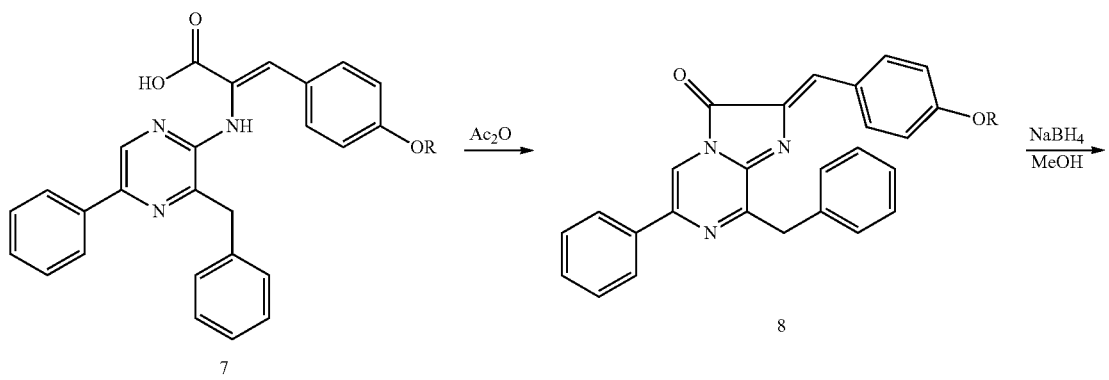

7

8

-continued

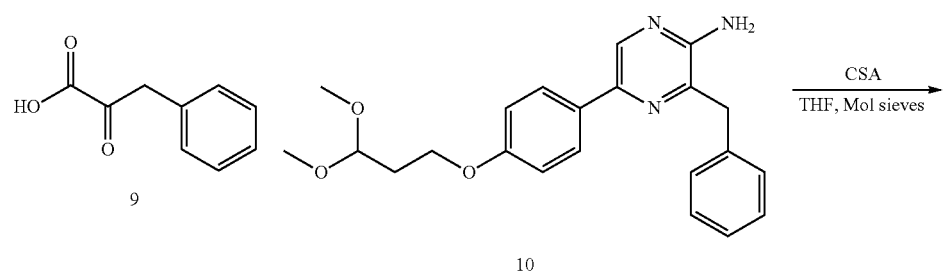

A mixture of 3-benzyl-5-phenylpyrazin-2-amine (6) (1 equiv), (E)-3-(4-((3,7-dimethylocta-2,6-dien-1-yl)oxy)phenyl)-2-oxopropanoic acid (5) (1.5 equiv) and camphor sulfonic acid (1.5 equiv) in THF is heated at reflux in the presence of molecular sieves until condensation of the starting materials is complete. The reaction mixture is diluted with ethyl acetate to 3 times its volume and washed with water and brine solution. After drying over sodium sulfate, the solvent is removed under vacuum and the residue containing compound 7 is dissolved in dry DMF. The resulting solution is treated with acetic anhydride (1.5 equiv) and pyridine (1.5 equiv) at room temperature. The progress of the reaction can be monitored by TLC, and once complete, the reaction mixture is cooled in an ice bath for several minutes before addition of a volume of water equal to the reaction volume. The resulting mixture is extracted with a suitable organic solvent (e.g. ethyl acetate), and the extracts are concentrated to provide compound 8. The material is dissolved in methanol and, after cooling to approximately 0° C., treated with sodium borohydride (5-10 equiv) in small portions until the product formation is complete. While still cold, the reaction mixture can be treated with acetic acid in an amount equivalent to the moles of hydride previously added, and the reaction mixture can be concentrated under vacuum. The residue can be triturated with water several times to give crude compound 3. This material can be purified using chromatography over silica gel.

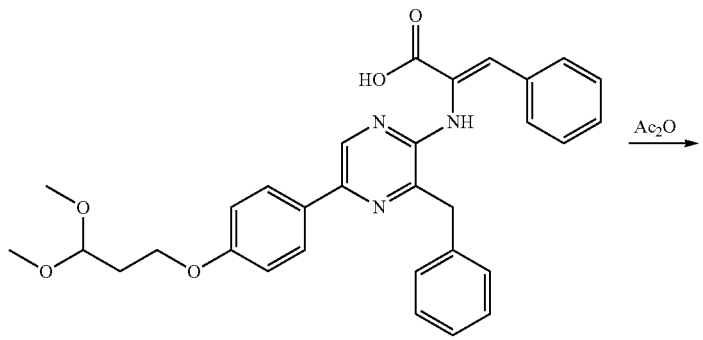

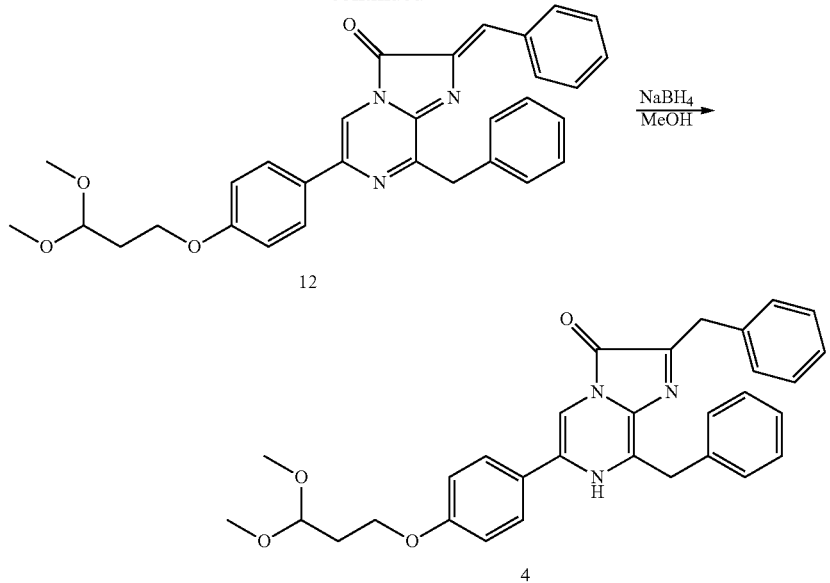

A mixture of 3-benzyl-5-(4-(3,3-dimethoxypropoxy)phenyl)pyrazin-2-amine (10) (1 equiv), 2-oxo-3-phenylpropanoic acid (9) (1.5 equiv) and camphor sulfonic acid (CSA) (1.5 equiv) in THF is heated at reflux in the presence of molecular sieves until condensation of the starting materials is complete. The reaction mixture is diluted with ethyl acetate to 3 times its volume and washed with water and brine solution. After drying over sodium sulfate, the solvent is removed under vacuum and the residue containing 11 is dissolved in dry DMF. The resulting solution is treated with acetic anhydride (1.5 equiv) and pyridine (1.5 equiv) at room temperature. The progress of the reaction can be monitored by TLC, and once complete, the reaction mixture is cooled in an ice bath for several minutes before addition of a volume of water equal to the reaction volume. The resulting mixture is extracted with a suitable organic solvent (e.g. ethyl acetate), and the extracts are concentrated to give compound 12. The material is dissolved in methanol and, after cooling to approximately 0° C., treated with sodium borohydride (5-10 equiv) in small portions until the formation of product is complete. While still cold, the reaction mixture is treated with acetic acid in an amount equivalent to the moles of hydride previously added, and the reaction mixture is concentrated under vacuum. The residue is triturated with water several times to give crude compound 4. This material can be purified using chromatography over silica gel.

Example 11

Measurement of NADH

A pro-coelenterazine substrate of the present invention for detecting diaphorase was used to measure the amount of NADH present in a sample. By combining NADH, diaphorase, the pro-coelenterazine substrate, and esterases, the NADH present in the sample was detected. The pro-coelenterazine substrate utilized by the diaphorase was converted to coelenterazine. The amount of coelenterazine generated was detected by an *Oplophorus* luciferase variant, and the luminescence generated is proportional to the amount of NADH present in the sample.

Figure 9:
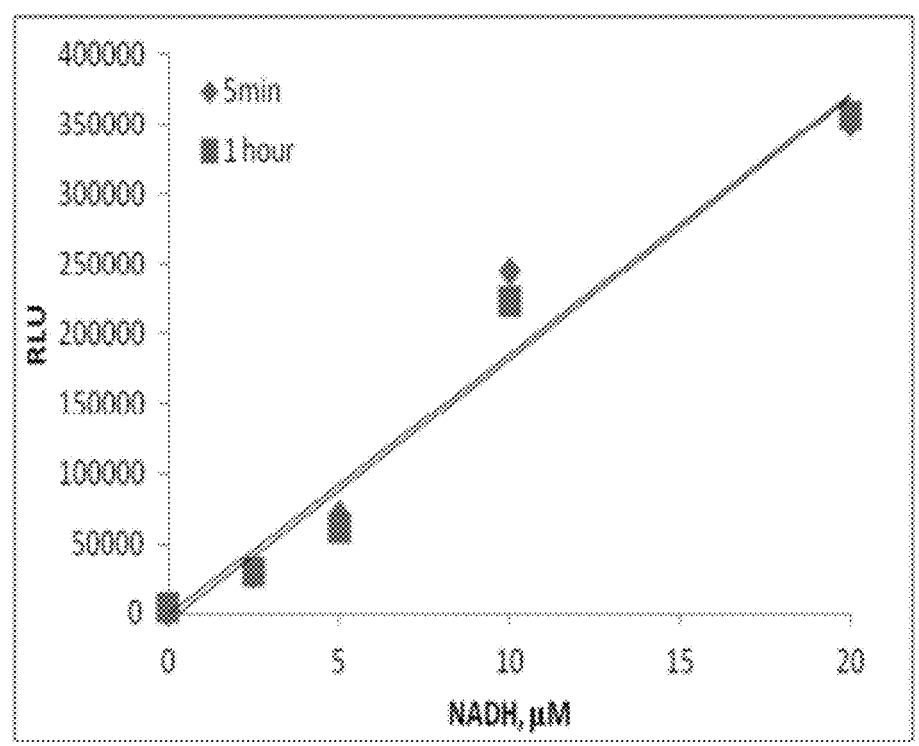
FIG. 9 shows detection of NADH using pro-coelenterazines according to the present invention.
Figure 10:
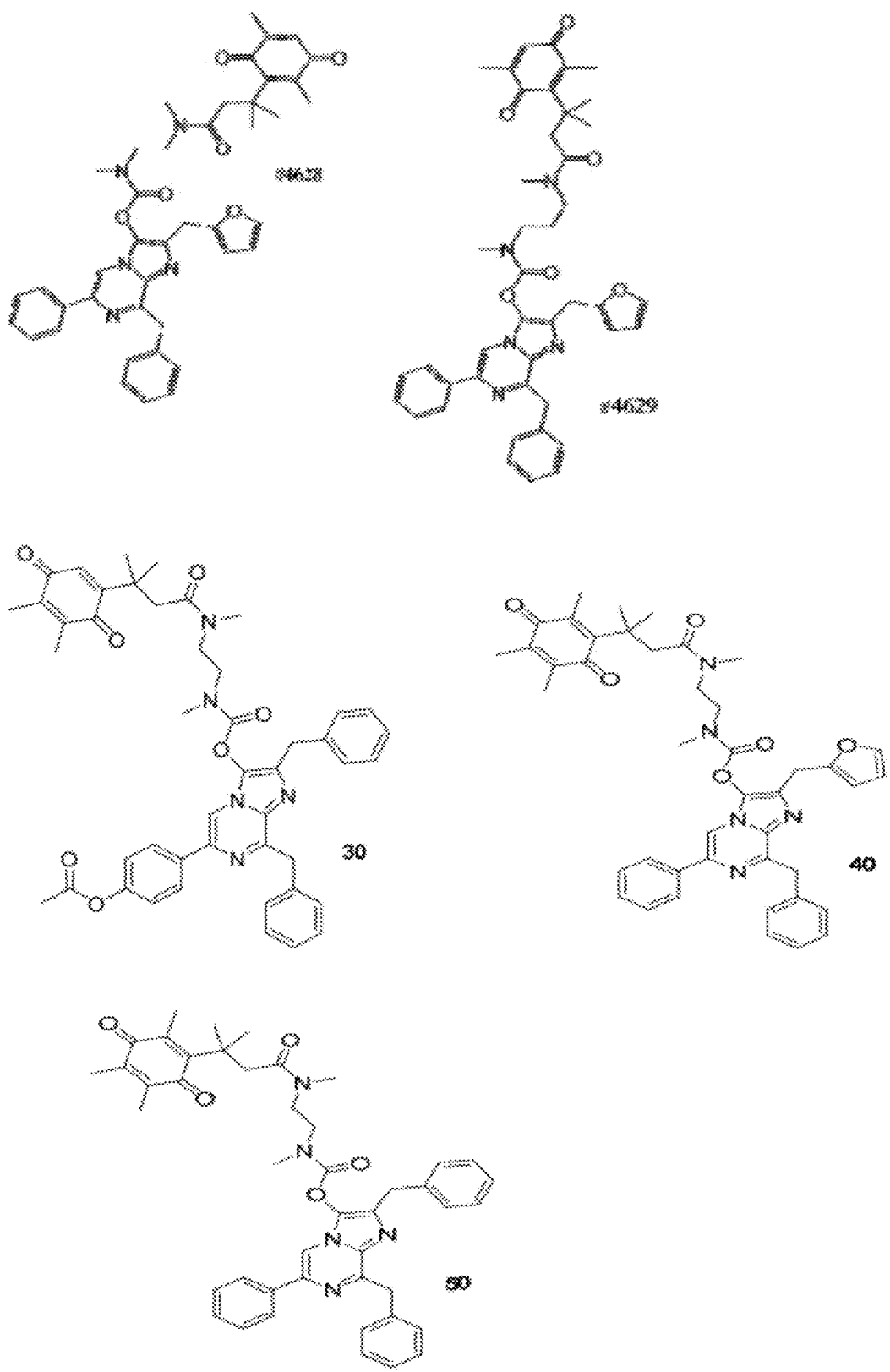
FIG. 10 shows other suitable pro-coelenterazine substrates according to the present invention.

For the assay, 10 μL NADH (titrated from 60 μM to 0 μM), 10 μL 12 U/mL diaphorase enzyme in PBS, 10 μL 165 U esterase in PBS and 10 μL 60 μM PBI-4600 in PBS were incubated at room temperature for 1 hour. After incubation, an *Oplophorus* luciferase detection reagent (100 mM MES pH 6, 1 mM CDTA, 150 mM KCl, 35 mM Thiourea, 1 mM DTT, 0.5% Tergitol and 0.05% Mazu) containing an *Oplophorus* luciferase variant (L27V) at a $10^9$ dilution was added. Luminescence was measured at 5 minutes and 1 hour (FIG. 9).

The data demonstrates that the compounds of the present invention can be used to measure NADH in a sample by detecting an enzyme which utilizes NADH.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. A compound of formula (II):

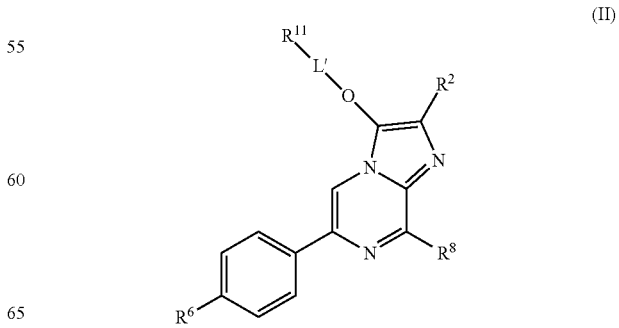

wherein R² is —(CH₂)ₙ-T or C₁₋₅ alkyl;
R⁶ is selected from the group consisting of —H, —OH, —NH₂, —OC(O)R or —OCH₂OC(O)R;
R⁸ is selected from the group consisting of

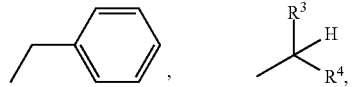

H or lower cycloalkyl;
R¹¹ is selected from the group consisting of a peptide containing from 2 to 35 amino acids, an amino acid, —O—R^A, —OC(O)O—R^A, —N(R^B)₂, or —NHC(O)OR^A;
wherein R³ and R⁴ are both H or both C₁₋₂ alkyl;
R^A is C₁₋₄ alkyl, substituted C₁₋₄ alkyl, —CH₂—R^c or —CH₂—V—R^c;
each R^B is independently —H or —R^A;
R^c is aryl, heteroaryl, substituted aryl or substituted heteroaryl;
L' is a direct bond or a linker, wherein the linker is selected from the group consisting of

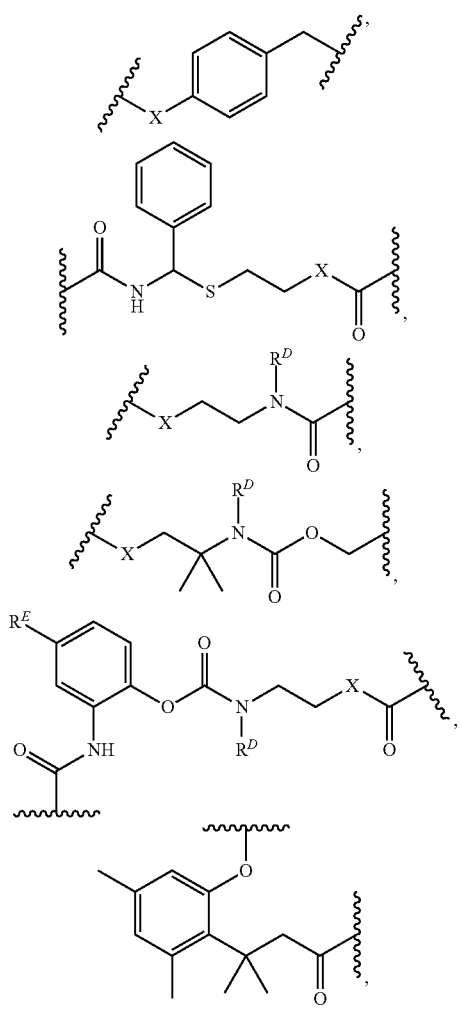

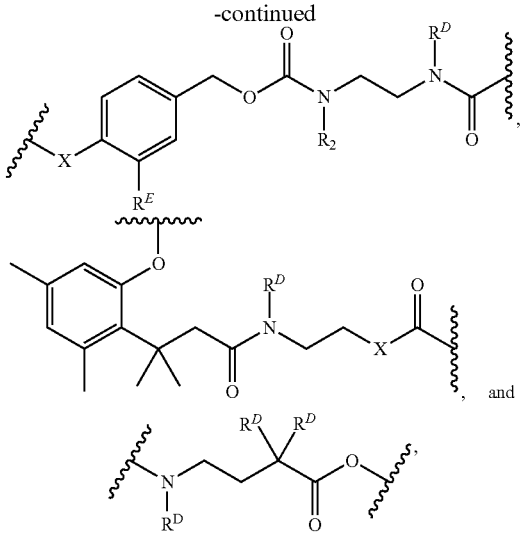

wherein each R^E is independently H, halogen or NO₂, each R^D is independently H or Me, and each X is independently NH, NMe, O or S;
n is 0 to 3;
each R is independently a C₁₋₇ alkyl;
T is aryl, heteroaryl, substituted aryl, substituted heteroaryl or cycloalkyl; and
V is —S— or —O—.

2. A compound according to claim 1, wherein R² is

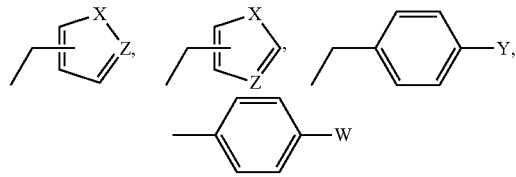

or C₂₋₅ straight-chain alkyl;
each X is independently —S—, —O— or —NH—;
Z is —CH— or —N—;
Y is —H or —OH;
W is —NH₂, halo, —OH, —NHC(O)R, —CO₂R; and
R is C₁₋₇ alkyl.

3. A compound according to claim 1, wherein R² is

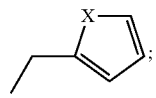

and X is O or S.

4. A compound according to claim 1, wherein R² is C₂₋₅ straight-chain alkyl.

5. A compound according to claim 1, wherein R⁸ is

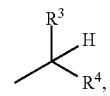

lower cycloalkyl or H, wherein $R^3$ and $R^4$ are both H or $C_{1-2}$ alkyl.

6. A compound according to claim 1, wherein $R^8$ is benzyl.

7. A compound according to claim 1, wherein V is S.

8. A method of detecting the presence or amount of an enzyme comprising:
   contacting a sample suspected of containing the enzyme with a compound according to claim 1; and
   detecting luminescence of the sample.

9. The method of claim 8, wherein the luminescence is quantified.

10. A method of detecting the presence of an enzyme in vivo comprising:
    administering a compound according claim 1 to a transgenic animal; and
    detecting luminescence.

11. A method of detecting the presence of an enzyme comprising:
    administering a compound according to claim 1 to an animal;
    obtaining a sample from the animal; and
    detecting luminescence of the sample.

12. A method of detecting a second enzyme in a sample suspected of containing more than one enzyme comprising
    contacting a sample suspected of containing more than one enzyme with a first compound according to claim 1;
    contacting the sample with a second compound according to claim 1; and
    detecting the luminescence of the sample; and
    wherein the first compound contains a substrate for a first enzyme and the second compound contains a substrate for a second enzyme.

13. A compound selected from the group consisting of:

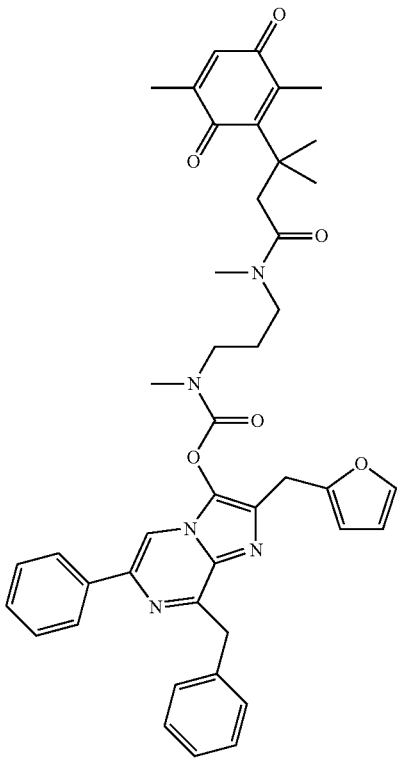

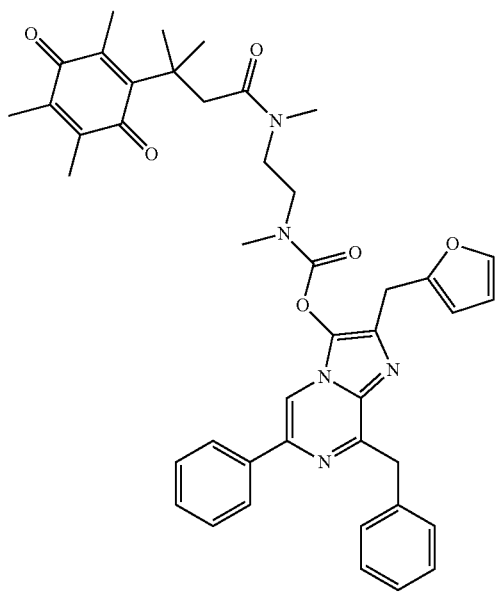
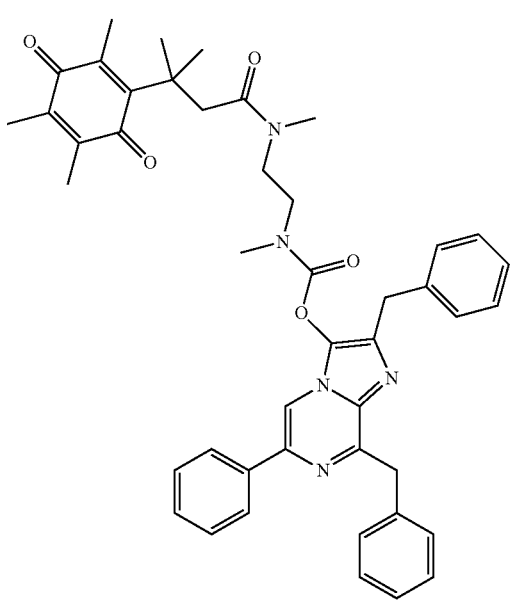
(25)
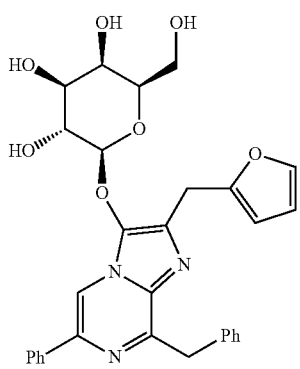
(26)
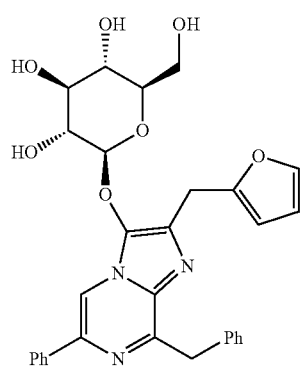
(27)
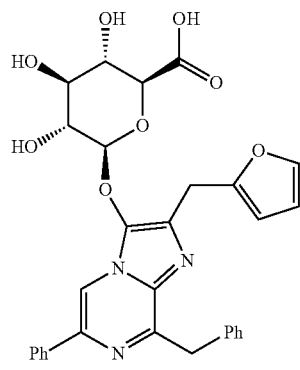
(28)
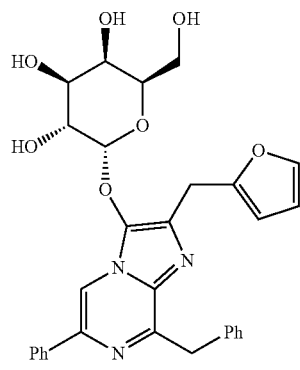
(29)
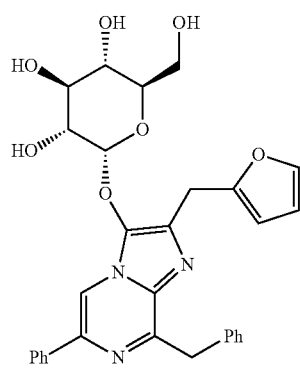

-continued

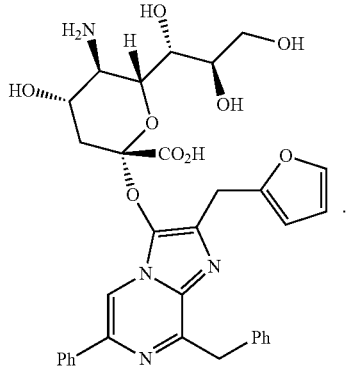
(30)

14. A compound of formula (II):

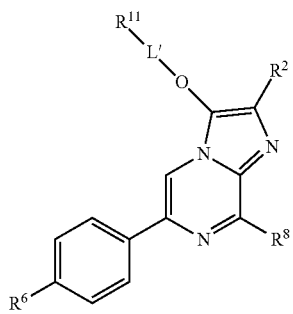
(II)

wherein R² is —(CH₂)ₙ-T or C₁₋₅ alkyl;

R⁶ is selected from the group consisting of —H, —OH, —NH₂, —OC(O)R or —OCH₂OC(O)R;

R⁸ is

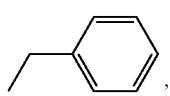,

R¹¹ is selected from the group consisting of a peptide having from 2 to 35 amino acids, an amino acid, a saccharide, —O—R$^A$, —OC(O)O—R$^A$, —N(R$^B$)₂, or —NHC(O)OR$^A$;

R$^A$ is C₁₋₄ alkyl, substituted C₁₋₄ alkyl, —CH₂—R$^c$ or —CH₂—V—R$^c$;

each R$^B$ is independently —H or —R$^A$;

R$^c$ is aryl, heteroaryl, substituted aryl or substituted heteroaryl;

L' is a direct bond or a linker, wherein the linker is selected from the group consisting of

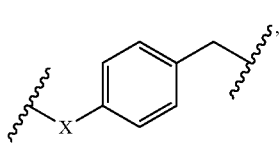

-continued

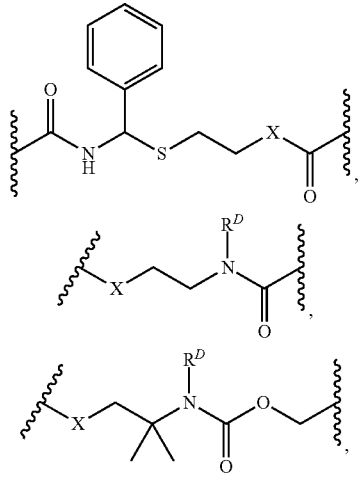

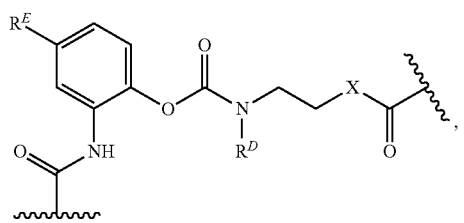

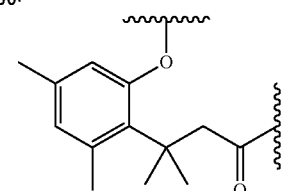

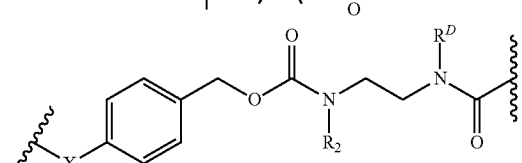

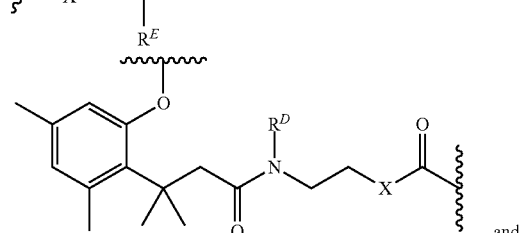, and

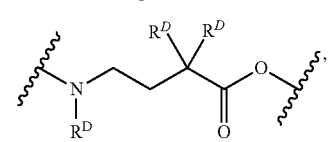

wherein each R$^E$ is independently H, halogen or NO₂, each R$^D$ is independently H or Me, and each X is independently NH, NMe, O or S;

n is 0 to 3;

each R is independently a C₁₋₇ alkyl;

T is heteroaryl, substituted heteroaryl or cycloalkyl; and

V is —S— or —O—.

15. A compound according to claim 14, wherein $R^2$ is

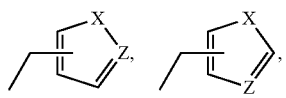

or $C_{2-5}$ straight-chain alkyl;
each X is independently —S—, —O— or —NH—;
Z is —CH— or —N—; and
R is $C_{1-7}$ alkyl.

16. A compound according to claim 14, wherein $R^2$ is

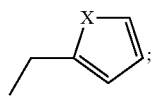

and
X is O or S.

17. A method of detecting the presence or amount of an enzyme comprising:
contacting a sample suspected of containing the enzyme with a compound according to claim 14; and
detecting luminescence of the sample.

18. The method of claim 17, wherein the luminescence is quantified.

19. A method of detecting the presence of an enzyme in vivo comprising:
administering a compound according claim 14 to a transgenic animal; and
detecting luminescence.

20. A method of detecting the presence of an enzyme comprising:
administering a compound according to claim 14 to an animal;
obtaining a sample from the animal; and
detecting luminescence of the sample.

21. A method of detecting a second enzyme in a sample suspected of containing more than one enzyme comprising contacting a sample suspected of containing more than one enzyme with a first compound according to claim 14;
contacting the sample with a second compound according to claim 14; and
detecting the luminescence of the sample; and
wherein the first compound contains a substrate for a first enzyme and the second compound contains a substrate for a second enzyme.

* * * * *

UNITED STATES PATENT AND TRADEMARK OFFICE
CERTIFICATE OF CORRECTION

PATENT NO. : 9,487,520 B2
APPLICATION NO. : 13/287519
DATED : November 8, 2016
INVENTOR(S) : Dieter H. Klaubert et al.

Page 1 of 1

It is certified that error appears in the above-identified patent and that said Letters Patent is hereby corrected as shown below:

In the Claims

In Claim 1, Column 34, Line 5, please delete the structure:

"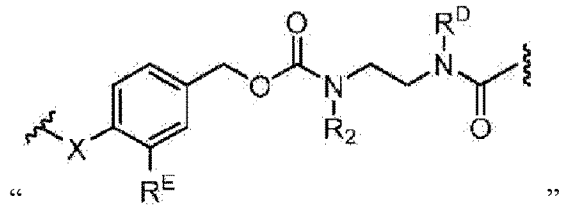"

And please replace it with the following structure:

--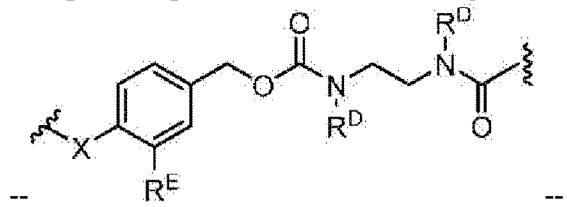--

Signed and Sealed this
Twenty-seventh Day of November, 2018

Andrei Iancu
*Director of the United States Patent and Trademark Office*